US010751527B2

(12) United States Patent
Wolf, II

(10) Patent No.: US 10,751,527 B2
(45) Date of Patent: Aug. 25, 2020

(54) DEVICE AND METHOD FOR PERCUTANEOUS PLACEMENT AND ANCHORING OF STIMULATING ELECTRODES IN SPINE

(71) Applicant: Erich W. Wolf, II, Lake Charles, LA (US)

(72) Inventor: Erich W. Wolf, II, Lake Charles, LA (US)

( * ) Notice: Subject to any disclaimer, the term of this patent is extended or adjusted under 35 U.S.C. 154(b) by 319 days.

(21) Appl. No.: 15/724,208

(22) Filed: Oct. 3, 2017

(65) Prior Publication Data
US 2018/0093094 A1    Apr. 5, 2018

Related U.S. Application Data

(60) Provisional application No. 62/403,492, filed on Oct. 3, 2016.

(51) Int. Cl.
| | |
|---|---|
| *A61N 1/05* | (2006.01) |
| *A61B 17/34* | (2006.01) |
| *A61B 17/68* | (2006.01) |
| *A61B 17/16* | (2006.01) |
| *A61B 17/86* | (2006.01) |
| *A61B 90/00* | (2016.01) |

(52) U.S. Cl.
CPC ........ *A61N 1/0558* (2013.01); *A61B 17/1671* (2013.01); *A61B 17/3403* (2013.01); *A61B 17/3472* (2013.01); *A61B 17/68* (2013.01); *A61B 17/1604* (2013.01); *A61B 17/8685* (2013.01); *A61B 2090/034* (2016.02)

(58) Field of Classification Search
CPC .............. A61N 1/0558; A61B 17/1671; A61B 17/3403; A61B 17/3468; A61B 17/3472; A61B 17/68
See application file for complete search history.

(56) References Cited

U.S. PATENT DOCUMENTS

| | | |
|---|---|---|
| 5,562,670 A | 10/1996 | Branemark et al. |
| 6,356,792 B1 | 3/2002 | Errico et al. |
| 6,778,861 B1 | 8/2004 | Liebrecht et al. |

(Continued)

FOREIGN PATENT DOCUMENTS

| | | |
|---|---|---|
| DE | 3942735 A1 | 6/1991 |
| WO | 2011150480 A1 | 12/2011 |

OTHER PUBLICATIONS

Holly, L.T., et al, "Percutaneous Placement of Posterior Cervical Screws Using Three-Dimensional Fluoroscopy," Spine (Mar. 1, 2006) 31(5):536-540.

(Continued)

*Primary Examiner* — Melanie R Tyson
(74) *Attorney, Agent, or Firm* — Schultz & Associates, P.C.

(57) ABSTRACT

A system and method for anchoring an electrode that stimulates a dorsal root ganglion. The anchoring device includes a screw, collet, and locking cap. The screw is inserted into bone of the pars interarticularis and the electrode is inserted through the screw and positioned next to the dorsal root ganglion for stimulation. The screw includes a recess that is shaped to fit the collet. The collet has flexible arms. When assembled, the locking cap forces the collet into the recess thereby moving the flexible arms inward radially, impinging on the electrode and holding the electrode in place adjacent the dorsal root ganglion.

15 Claims, 24 Drawing Sheets

(56) References Cited

U.S. PATENT DOCUMENTS

| | | |
|---|---|---|
| 7,657,308 B2 | 2/2010 | Miles |
| 8,070,785 B2 | 12/2011 | Biscup |
| 8,075,630 B2 | 12/2011 | Ricci et al. |
| 8,348,983 B2 | 1/2013 | Neubardt |
| 8,380,319 B2 | 2/2013 | Berger |
| 8,486,119 B2 | 7/2013 | Bourlion |
| 8,600,495 B2 | 12/2013 | Gielen et al. |
| 8,738,144 B2 | 5/2014 | Schneider |
| 9,205,260 B2 | 12/2015 | Kim et al. |
| 9,232,906 B2 | 1/2016 | Wolf |
| 9,259,248 B2 | 2/2016 | Leuthardt et al. |
| 9,387,319 B2 | 7/2016 | Pianca |
| 9,439,694 B2 | 9/2016 | Kraus et al. |
| 9,474,900 B2 | 10/2016 | Kraus |
| 9,579,222 B2 | 2/2017 | Branemark et al. |
| 9,737,233 B2 | 8/2017 | Londot |
| 2004/0243207 A1 | 12/2004 | Olson et al. |
| 2010/0036467 A1 | 2/2010 | Kraus et al. |
| 2010/0106198 A1 | 4/2010 | Adcox et al. |
| 2010/0298886 A1 | 11/2010 | Kraus et al. |
| 2015/0057564 A1 | 2/2015 | Kim |
| 2016/0038205 A1 | 2/2016 | Smith |
| 2016/0199112 A1 | 7/2016 | Kim |
| 2017/0021180 A1 | 1/2017 | Datta |

OTHER PUBLICATIONS

Sairyo, K., et al, "Minimally invasive technique for direct repair of pars interarticularis defects in adults using a percutaneous pedicle screw and hook-rod system," Journal of Neurosurgery: Spine (May 2009) 10(5):492-495.

North, R.A., et al, "Spinal Cord Stimulation Electrode Design: A Prospective, Randomized, Controlled Trial Comparing Percutaneous with Laminectomy Electrodes: Part II—Clinical Outcomes," Neurosurgery (Nov. 1, 2005) 57(5):990-996.

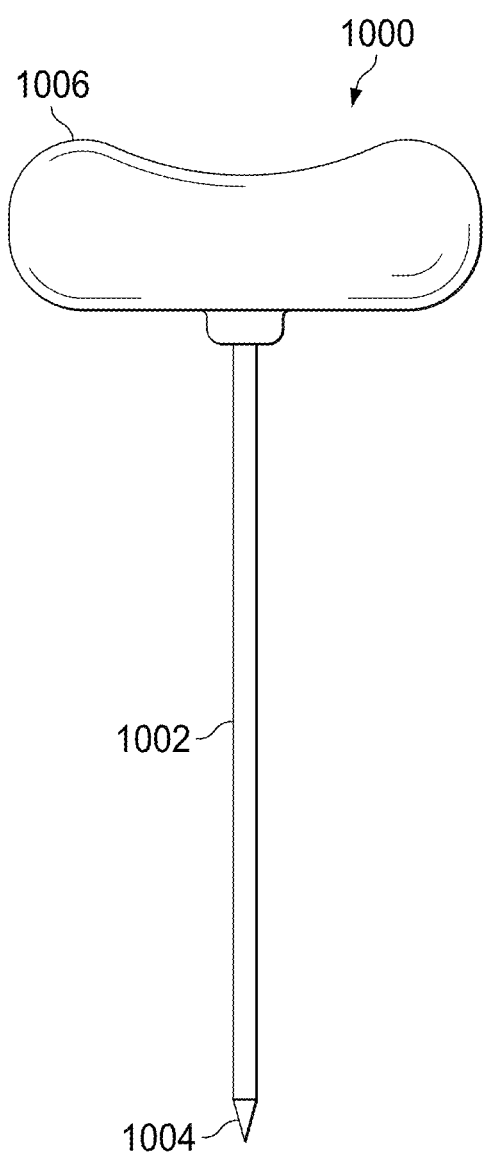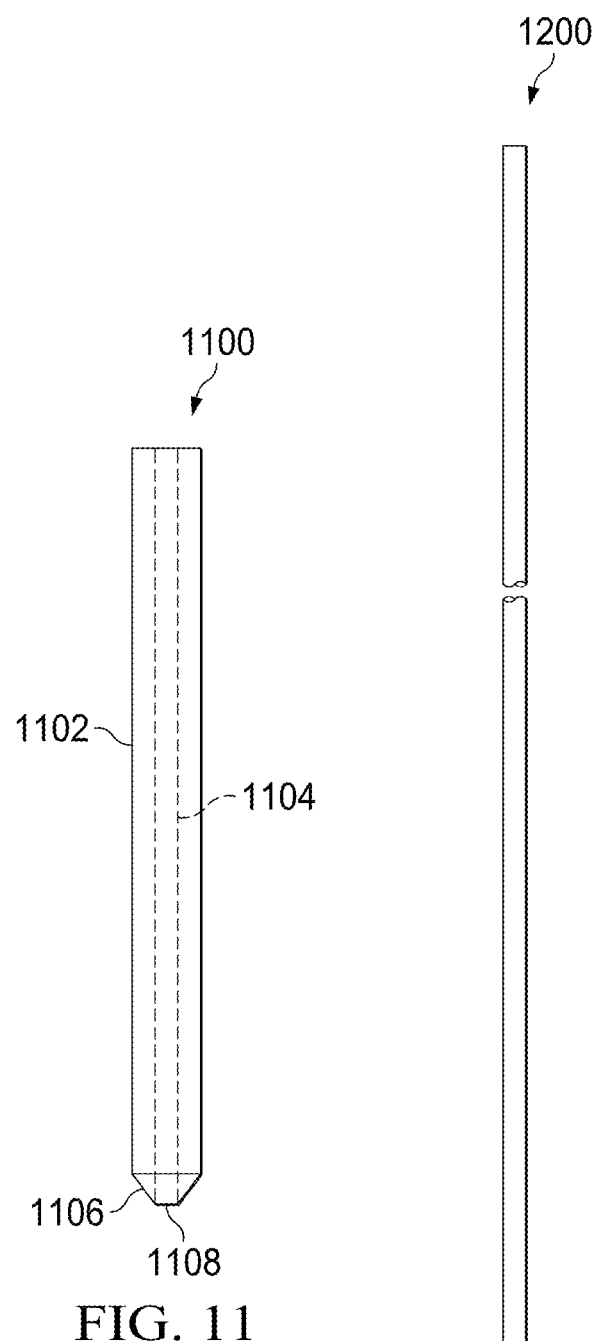
FIG. 10
FIG. 11
FIG. 12

DEVICE AND METHOD FOR PERCUTANEOUS PLACEMENT AND ANCHORING OF STIMULATING ELECTRODES IN SPINE

CROSS-REFERENCE TO RELATED APPLICATIONS

This application claims priority to U.S. Provisional Application No. 62/403,492 filed Oct. 3, 2016, which is incorporated herein by reference in its entirety to provide continuity of disclosure.

BACKGROUND OF THE INVENTION

Mechanical compression or injury to spinal nerves with resulting radicular pain can develop in response to a variety of conditions, including spondylolisthesis, osteoarthritis, and degenerative disc disease, among others. Nerve root irritation can also result in numerous symptoms aside from the radicular pain, including both sensory and motor deficiencies, such as numbness of the extremities, weakness, and difficulty with or loss of dexterity and muscle control.

One method for controlling pain resulting from irritation of a nerve root is electrical stimulation of the dorsal nerve rootlet and associated dorsal root ganglion, effected by an electrode array implanted peripheral to the dorsal rootlet. The dorsal rootlet transmits sensory signals, and stimulation of the dorsal rootlet can alleviate painful sensations without interfering with motor functions, which are transmitted through the adjacent ventral rootlet.

The dorsal root ganglion is located along the dorsal rootlet and contains the cell bodies of the neurons whose axons traverse the dorsal root. Stimulation of the dorsal root ganglion is a promising treatment for neuropathic pain. Research shows that over half of patients with chronic back pain see a reduction in symptoms with nerve stimulation, or neuromodulation, procedures.

To maximize the efficacy of dorsal root stimulation, implantation of the electrode array should be proximate to the dorsal root ganglion. Location at greater distances requires increased amounts of energy to be delivered to the electrode array to achieve the desired stimulation, which depletes energy sources more quickly. Prior art solutions, such as implantation of an electrode array on the exterior of the vertebrae running parallel to the spinal column, suffer from this problem. Furthermore, location outside the spinal vertebrae leaves the electrical stimulation signal subject to dissipation due to bulk conductivity of the surrounding soft tissues and cerebrospinal fluid.

The technical skill required to properly locate the electrode adjacent the dorsal root ganglia presents a challenge because of the anatomical orientation of the nerve rootlet and dorsal root ganglion within the intervertebral foramen. Additionally, the site of the ganglia varies depending on the location of the vertebrae of a single patient. For example, one survey found the location of the dorsal root ganglia in the fourth lumbar spine to be intraspinal ("IS") in approximately 6% of patients, intraforminal ("IF") in approximately 48% of patients, and extraforminal ("EF") in 41% (5% were not identified). In the fifth lumbar spine, the same population had 10% IS, 75% IF, and 6% IS (with 9% not identified) dorsal root ganglia.

Prior art techniques address this problem by percutaneously injecting the electrode through the intervertebral foramen via a needle, laying it alongside the spinal nerve root. However, this technique leaves the electrode suspended in the intervertebral foramen without firm fixation. Hence, the electrode array is prone to migration, which both diminishes the efficacy of the stimulation technique and can cause other complications necessitating surgical correction of the migration or removal of the electrode array.

Percutaneous injection is also not an ideal solution because it carries with it all the risks, costs, and time constraints normally associated with surgery. Further, surgery may not be an option for certain patients because of risk factors such as age, clotting, prior injuries, and pre-existing epidural scars.

The problem of electrode array migration has been addressed by other prior art techniques, but has not been adequately resolved. For example, prior art techniques to anchor the electrode include an anchoring hook that is engaged in the fibrous fascia layer surrounding the nerve root. The anchoring hook must pierce the nerve fascia layer. But, piercing the nerve fascia layer with a hook presents risk of nerve damage. Migration also remains a problem with this technique.

U.S. Patent Publication No. 2017/0021180 to Datta discloses a method for implantation of a neural stimulator comprised of electrodes attached to a generator. The electrodes are connected to the generator via a subcutaneous lead with connector plugs. However, the method anchors the electrode to the soft tissue near the targeted nerve, which leaves the electrode susceptible to migration.

U.S. Patent Publication No. 2016/0199112 to Kim discloses a medical insertion apparatus comprised of a screw nail body to be implanted in a boney structure that includes an electrode. The screw nail body includes an electrode connected to a lead which runs along the length of the screw nail body either inside a cavity or along the outside edge, or a combination thereof. The position of the electrode is fixed at the terminal end of the screw nail body, requiring the screw nail body to be located immediately peripheral to the targeted nerve, which is not always possible when targeting the dorsal root ganglion. Furthermore, the screw nail body must be seated perpendicularly to the surrounding bone, prohibiting an electrode position parallel to the nerve root. Alternatively, using an array of electrodes that extends beyond the tip of the screw nail body leaves the array adrift in the epidural space, with no way to position the array precisely and no way to control electrode migration.

U.S. Pat. No. 6,356,792 to Errico, et al. discloses an assembly for securing an electrode inside a patient's skull. A skull port member is affixed to the skull. An electrode is placed inside the skull and the connecting lead is run through the skull port member. The electrode is secured by a mechanism that seats in the skull port member and crimps the connecting lead. However, the electrode is susceptible to movement when the operator inserts the lead-locking mechanism into the skull port member and crimps the connecting lead. The nature of the mechanism also limits the possible materials and possible sizes of the assembly, as thinner and lighter materials in the connecting lead would be likely to break when crimped in place by the lead locking mechanism. Furthermore, the design is ill-suited for use in the spine, as there is no way to position the electrode perpendicular to the direction of the skull port member, which is desirable for stimulation of spinal nerves.

U.S. Pat. No. 9,737,233 to Londot discloses an assembly having a pedicle screw with an electrically-conductive longitudinal member that is used to propagate a signal along the exterior of the pedicle screw. However, the assembly does not allow for placement of the electrode beyond the pedicle screw and limits locations to which electrical stimulation can be applied.

U.S. Pat. No. 9,579,222 to Branemark, et al. discloses a percutaneous gateway for transmission of signals from a patient's nervous system to a robotic prosthesis. The system discloses an apparatus for mounting a prosthesis and preserving the percutaneous transmission of signals with appropriate seals to prevent infection after long-term use, as well as use with stimulating electrodes that may optionally be implanted. However, the system does not disclose a method for locating the electrodes relative to targeted nerves, anchoring the position of the electrodes, or implantation in the spine.

Hence, there remains a need for an electrode array and implantation technique that can reliably locate the array within close proximity to the dorsal root ganglion, regardless of the ganglion site, and effectively anchor the array in place to reduce or eliminate future migration.

SUMMARY OF THE INVENTION

This disclosure provides for anchoring an electrode that stimulates a dorsal root ganglion. The electrode is anchored to the bone of the pars interarticularis using a set of tools that implant an anchoring device.

The disclosure further provides a device and method for percutaneous placement of a stimulating electrode into the spine using minimally-invasive surgery (MIS) techniques. The disclosure also provides a method for anchoring the electrode, which is resistant to migration. The disclosure also provides a method of electrode implantation accurately even in the presence of a pre-existing epidural scar. Reduced radiation from fluoroscopy for the technician is also anticipated.

A preferred embodiment consists of a cannulated anchoring screw which is placed fluoroscopically into the pars interarticularis using MIS techniques. A hole is drilled through the pars either under fluoroscopy or with the aid of electrophysiological monitoring of the nerve root. A pliable percutaneous lead with nickel-titanium alloy "memory metal" stylet is then advanced fluoroscopically through the anchor screw along the course of the nerve root to lay parallel to the dorsal root ganglion. The stylet is removed and a locking cap is deployed over the screw to anchor the electrode array.

The disclosure also provides a preferred set of tools, that when used together, allow for implanting the anchoring device and electrode adjacent the dorsal root ganglion and anchoring it permanently to the pars interarticularis.

BRIEF DESCRIPTION OF THE DRAWINGS

FIG. 10 is a view of a preferred embodiment of a needle used with a preferred embodiment of an anchoring method.

FIG. 11 is a view of a preferred embodiment of a guide tube used with a preferred embodiment of an anchoring method.

FIG. 12 is a view of a preferred embodiment of a guidewire used with a preferred embodiment of an anchoring method.

DETAILED DESCRIPTION

Figure 1:
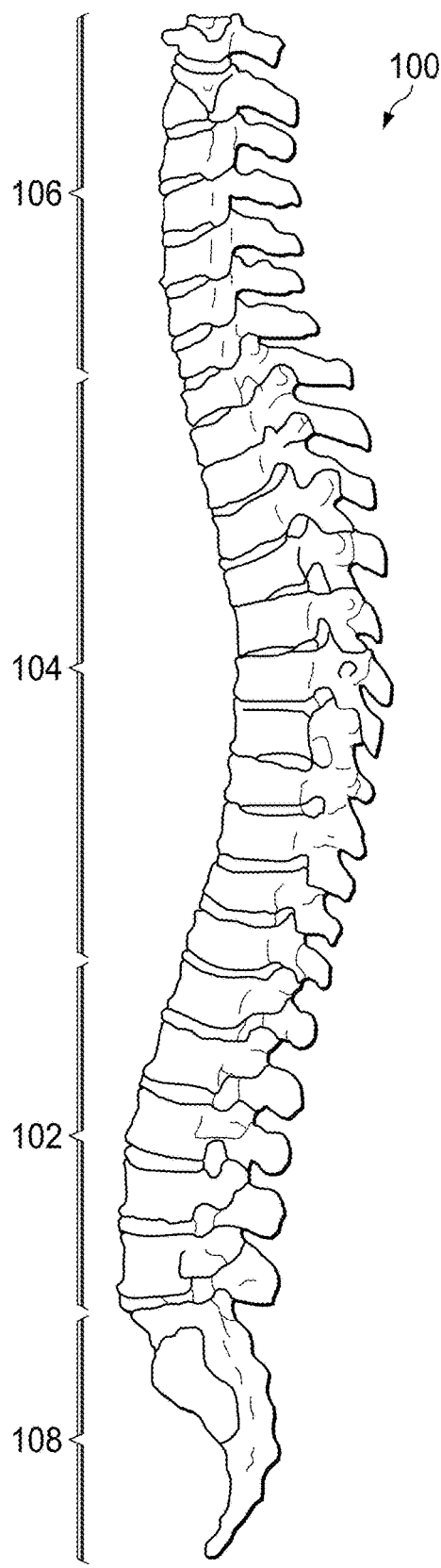
FIG. 1 is a median view of the human spine, showing the different types of vertebrae and their approximate location.

FIG. 1 shows a drawing of the human spine including spinal column 100. Spinal column 100 is comprised of a number of vertebrae, categorized into four sections, the lumbar vertebrae 102, the thoracic vertebrae 104, the cervical vertebrae 106 and the sacral vertebrae 108. Starting at the top of the spinal column, cervical vertebrae 106 include the 1st cervical vertebra (C1) through 7th cervical vertebra (C7). Just below the 7th cervical vertebra is the first of twelve thoracic vertebrae 104 including the 1st thoracic vertebra (T1) through 12th thoracic vertebra (T12). Just below the 12th thoracic vertebrae 104, are five lumbar vertebrae 102 including the 1st lumbar vertebra (L1) through 5th lumbar vertebra (L5). The 5th lumbar vertebra is attached to the sacral vertebrae 108 (S1 to S5), the sacral vertebrae 108 being naturally fused together in the adult.

Figure 2:
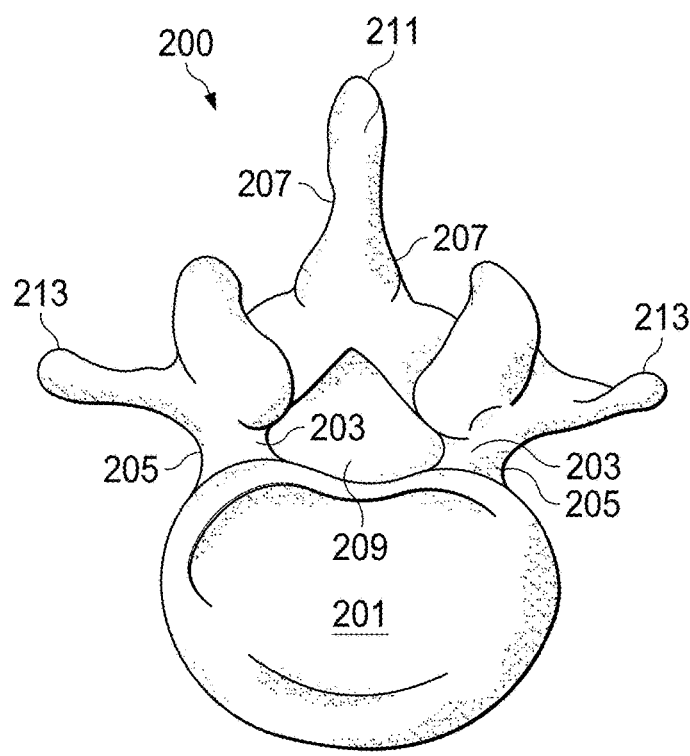
FIG. 2 is an axial view of a lumbar vertebra, showing the various bone features.

FIG. 2 shows an axial view of representative lumbar vertebrae 102. Representative lumbar vertebra 200 has a number of features which are shared with the thoracic vertebrae 104 and cervical vertebrae 106, although the feature thicknesses and shapes may vary. The thick oval segment of bone forming the anterior aspect of lumbar vertebra 200 is the vertebral body 201. Vertebral body 201 is attached to a bony vertebral arch 203 through which the neural elements run. Vertebral arch 203, forming the posterior of lumbar vertebra 200, is comprised of two pedicles 205, which are short stout processes that extend from the sides of vertebral body 201, and two laminae 207, the broad flat plates that project from pedicles 205 and join in a triangle to form a hollow archway, the spinal canal 209. Spinous process 211 protrudes from the junction of laminae 207. Transverse processes 213 project from the junction of pedicles 205 and laminae 207. The structures of the vertebral arch protect the spinal cord and/or spinal nerves that run through the spinal canal.

Figure 3:
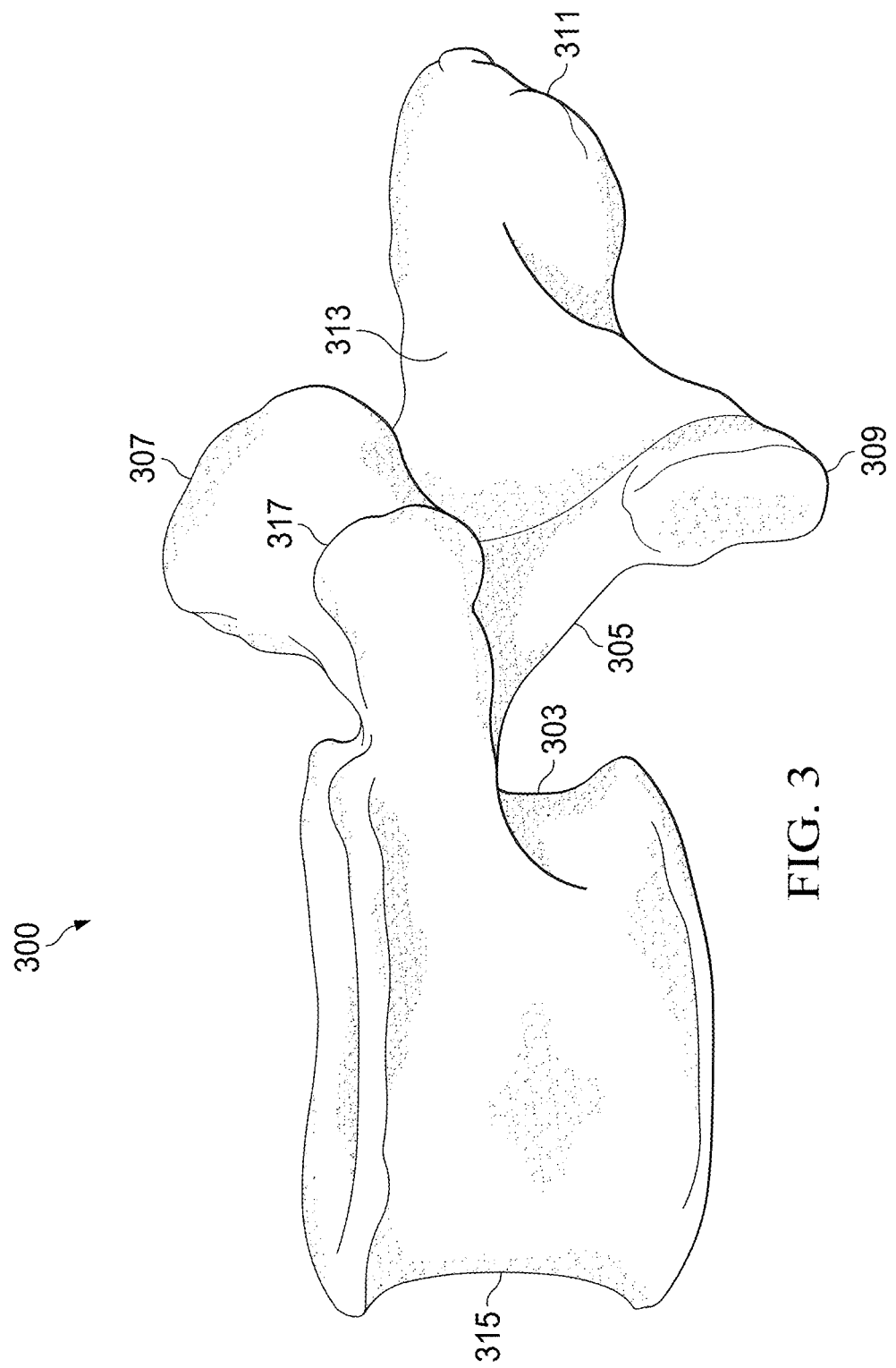
FIG. 3 is a sagittal view of a lumbar vertebra, showing the structure and foramen where spinal nerves are located.

In FIG. 3, a representative lumbar vertebra 300 is shown from a lateral view. Lumbar vertebra 300 has a number of structural features enabling it to house spinal nerves and connect with the vertebrae superior and inferior to it. Interior vertebral notch 303 aligns with the vertebra inferior to lumbar vertebra 300 to form intervertebral foramen 305. Lumbar vertebra 300 articulates with adjacent vertebra via the superior articular process 307 and inferior articular process 309. The spinous process 311 protrudes from the junction of the laminae. The pars interarticularis 313 is the thin wall of bone located between the superior articular process 307 and inferior articular process 309. In most cases, the minimum depth of the Pars is about 4 mm, but can be as much as 8 mm, depending on the patient and the vertebral position. Lumbar vertebra 300 joins to superior and inferior vertebrae by discs that attach superior and inferior to the vertebral body 315. Transverse processes 317 protrude laterally from lumbar vertebra 300.

Figure 4A:
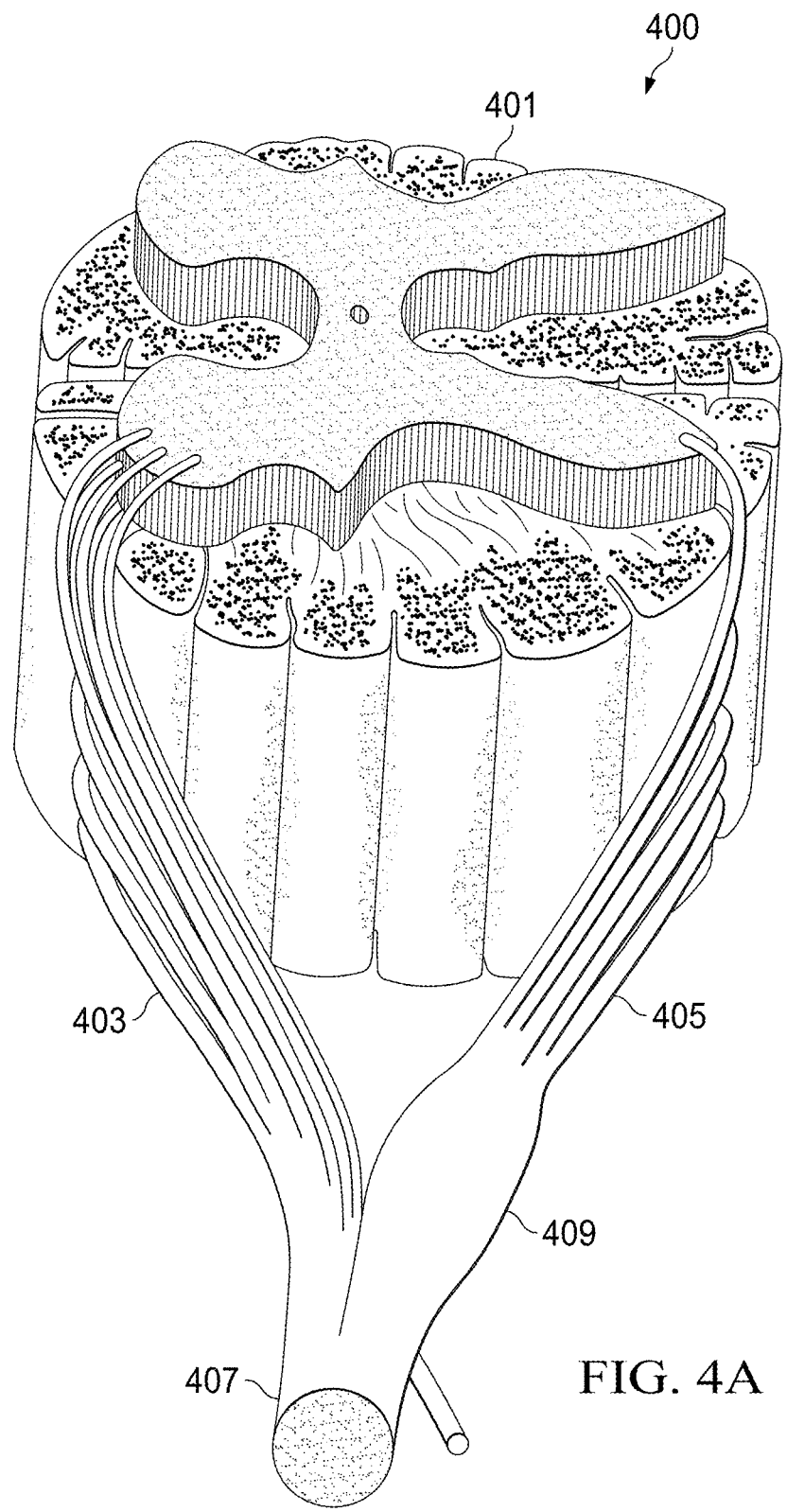
FIG. 4A depicts the attachment of the nerve roots to the spinal cord.

In FIG. 4A, a representative spinal cord segment 400 is shown in axial cross-section. The nerve structures are housed in the foramen shown in FIG. 3. Spinal cord 401 is situated in the vertebral foramen. Ventral root 403 and dorsal root 405 join to form spinal nerve root 407, which routes through intervertebral foramen. Dorsal root ganglion 409 is located along dorsal root 405.

One of the challenges faced by traditional spinal nerve stimulation techniques is positioning the electrode near the dorsal root ganglion. Maximum efficacy is achieved when the electrode is positioned adjacent to the dorsal root ganglion 409. However, the position of dorsal root ganglion 409 varies from patient to patient, with some dorsal root ganglia being lateral to the pedicle, outside the intervertebral foramen 305 while others are located medial to the pedicle 205.

Figure 4B:
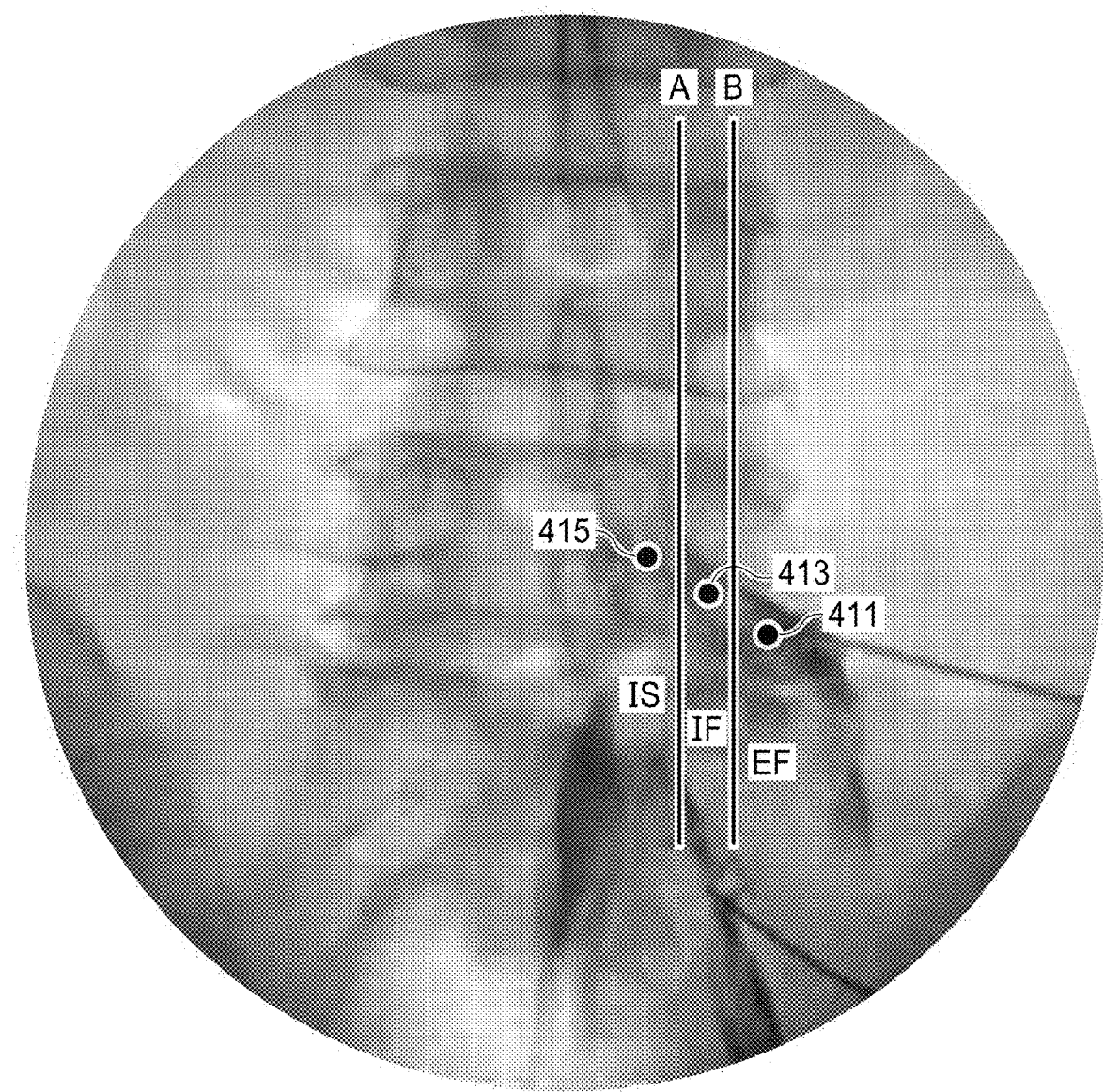
FIG. 4B is a frontal X-ray image of a patient's lumbar region, showing the possible locations of the dorsal root ganglion.

In FIG. 4B, an X-ray image of the lower lumbar spine is shown. Three dots show possible locations of the dorsal root ganglion 409. Position 411 shows the extraforamenal site (EF), located outside the intervertebral foramen 305. Position 413 shows the intraforamenal site (IF), located inside the intervertebral foramen 305. Position 415 shows the intraspinal site (IS), located within the vertebral foramen.

Figure 5:
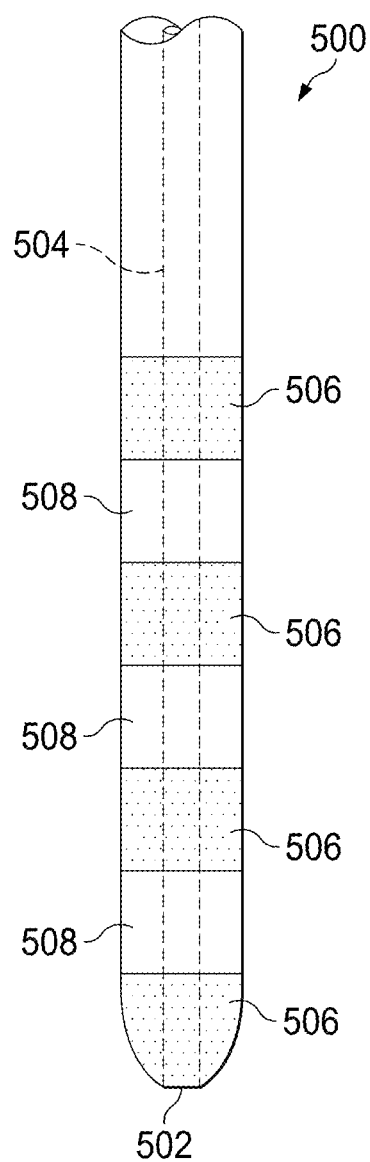
FIG. 5 is a view of a preferred embodiment of an electrode array that is used with an anchoring device.

Referring to FIG. 5, electrode 500 is a stimulating electrode array that contains one or more electrodes at distal tip 502. The interior of electrode 500 has a stylet channel 504 along a central axis to facilitate directional control of electrode 500 insertion. The electrode array includes annular electrode contacts 506 and annular insulating bands 508. In a preferred embodiment, the electrode is comprised of a pellethane or silastic outside sheeth with platinum-iridium electrode contacts. Wires (not shown) proceed through the stylet channel and connect the electrode array to a current source to supply stimulation once the electrode is firmly implanted.

Figure 6A:
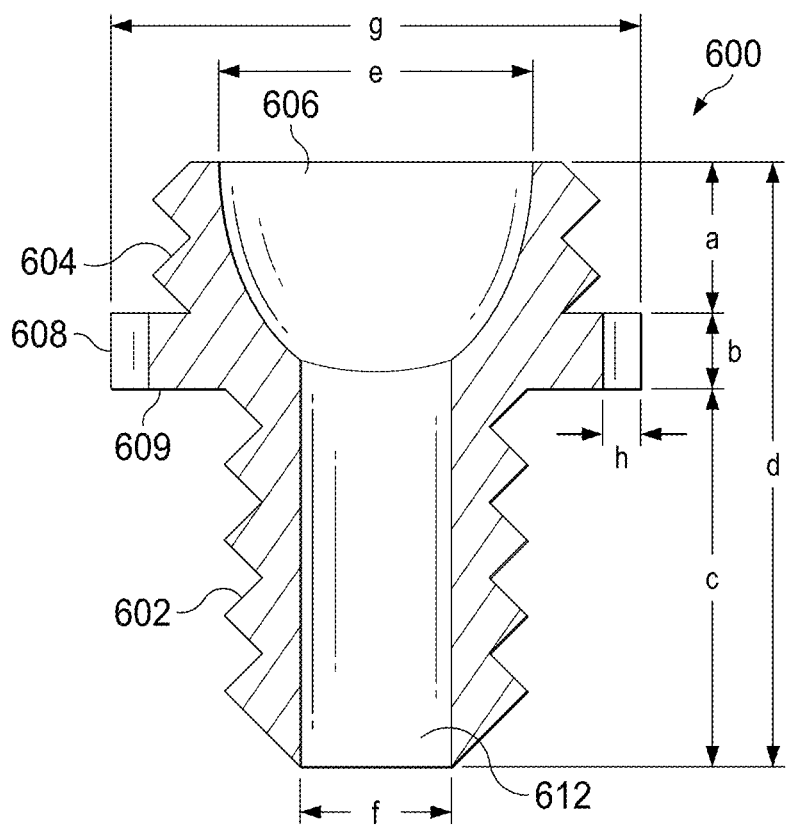
FIG. 6A is a cross section view of a screw of a preferred embodiment of an anchoring device.
Figure 6B:
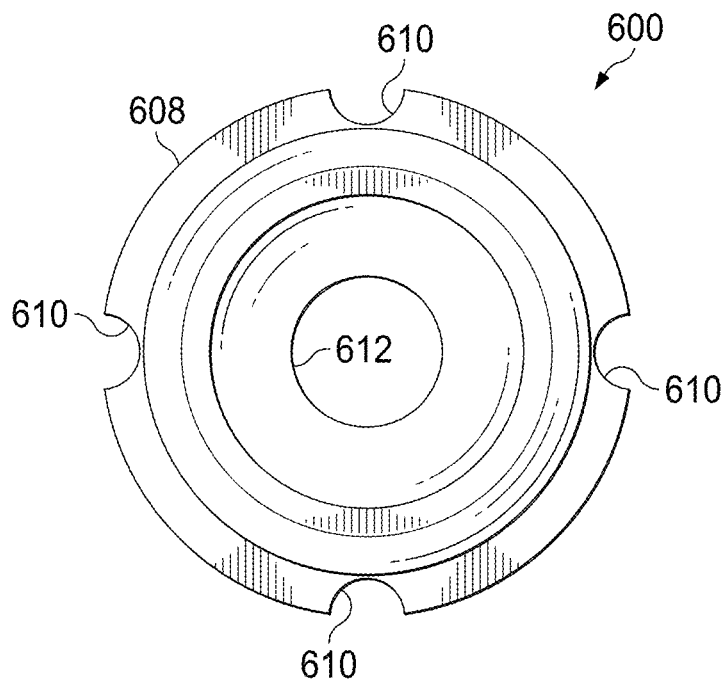
FIG. 6B is a top view of a preferred embodiment of an anchoring device.

Referring then to FIGS. 6A and 6B, a preferred embodiment of cannulated locking screw 600 of an anchoring device, will be described. Screw 600 has self-tapping right-handed threads 602 on its exterior. Flange 608 is positioned above the threads and forms a cylindrical shelf which functions to limit the depth that screw 600 can penetrate into the bone and to seat the screw against the bone surface. Flange 608 contains four detent indentions 610 which engage insertion tool 1400, which will be later described. In a preferred embodiment, underside 609 of flange 608 can be knurled to increase the friction between the flange and the bone surface. Screw 600 contains a recess 606 which engages collet 700 to anchor electrode 500 within lumen 612 of screw 600, lumen 704 of collet 700, and lumen 804 of locking cap 800. In a preferred embodiment, the recess is elliptical in shape, having a minor radius of about 2 mm and a major radius of about 3 mm. Left-handed threads 604 allow screw 600 to be attached and secured to locking cap 800. Screw 600 is preferably composed of titanium or an alloy thereof. In a preferred embodiment, the diameter "g" of flange 608 is about 10 mm, with the largest diameter "e" of recess 606 starting at about 6 mm and narrowing to match the 2 mm diameter "f" of lumen 612. The total height "d" of screw 600 is about 10 mm, with right-handed threads 602 running for a distance "c" of 5 mm, separated from the left-handed threads 604 having a height "a" of about 3 mm by the flange 608 having a height "b" of about 2 mm. Other dimensions can be envisioned to accommodate differing surgical conditions.

Figure 6C:
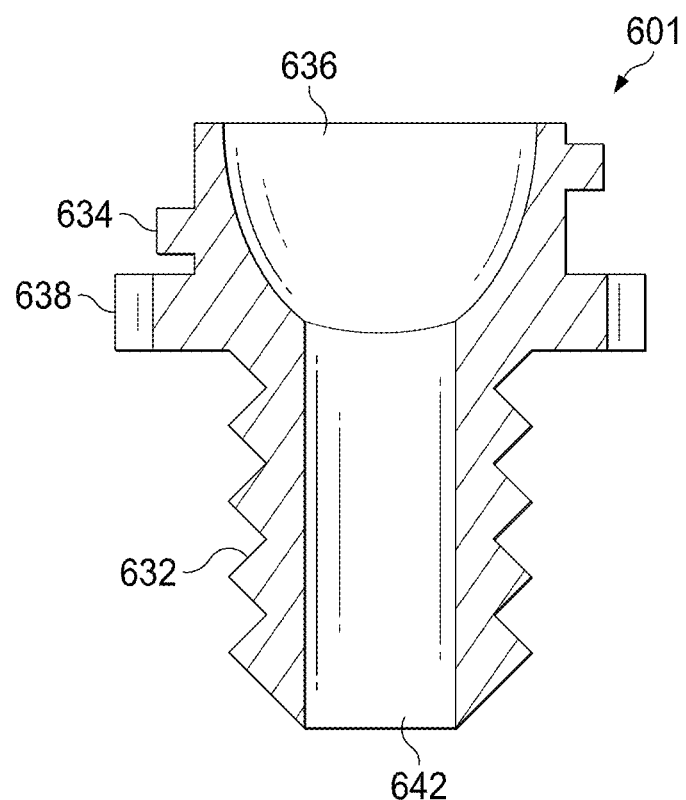
FIG. 6C is a cross section view of a screw of an alternate embodiment of an anchoring device.
Figure 6D:
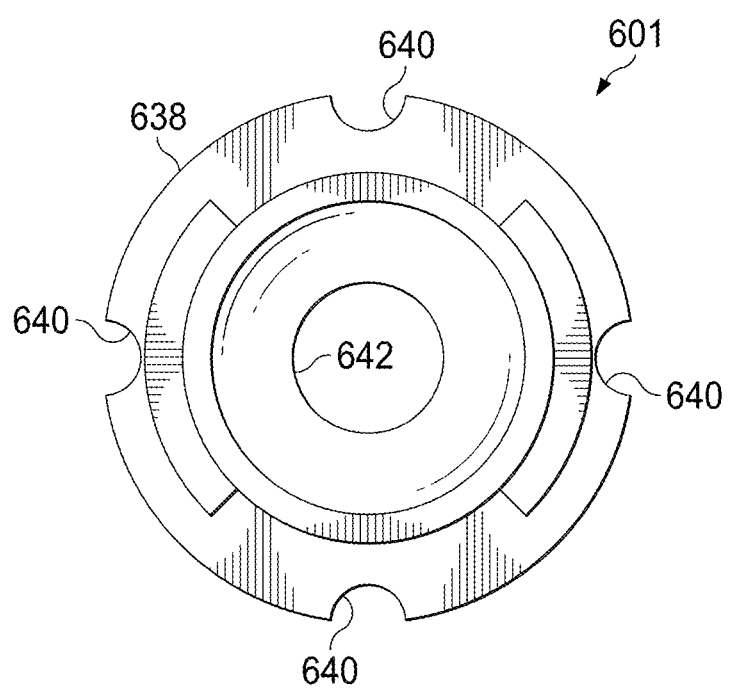
FIG. 6D is a top view of an alternate embodiment of an anchoring device.

Referring to FIGS. 6C and 6D, an alternate embodiment of cannulated locking screw 601 of an anchoring device will be described. Locking screw 601 has self-tapping right-handed threads 632. Flange 638 is positioned adjacent the threads and limits the depth that locking screw 601 can penetrate into the bone. Flange 638 contains four detent indentions 640 which engage insertion tool 1400. Locking screw 601 contains a recess 636 which engages collet 700 to anchor electrode 500 within lumen 642 of locking screw 601, lumen 704 of collet 700, and lumen 804 of locking cap 801. Bayonet mount 634 allows locking screw 601 to be attached and secured to locking cap 800 by 60° of rotation, as will be further described. The bayonet mount may be used instead of the threads between the locking screw and the locking cap in the various embodiments. Locking screw 601 is preferably composed of titanium an alloy thereof or a suitable medical plastic.

Figure 6E:
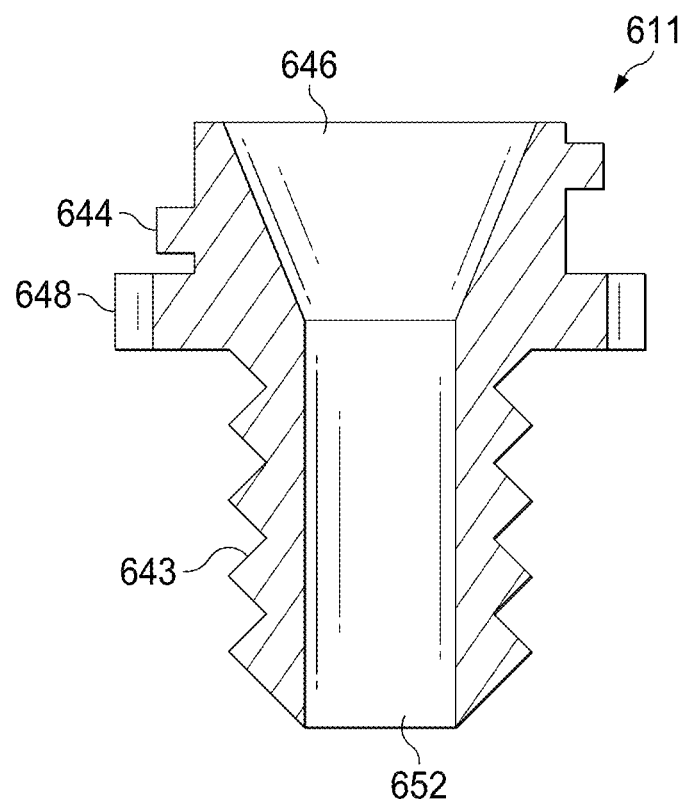
FIG. 6E is a cross section view of an alternate embodiment of an anchoring device.
Figure 6F:
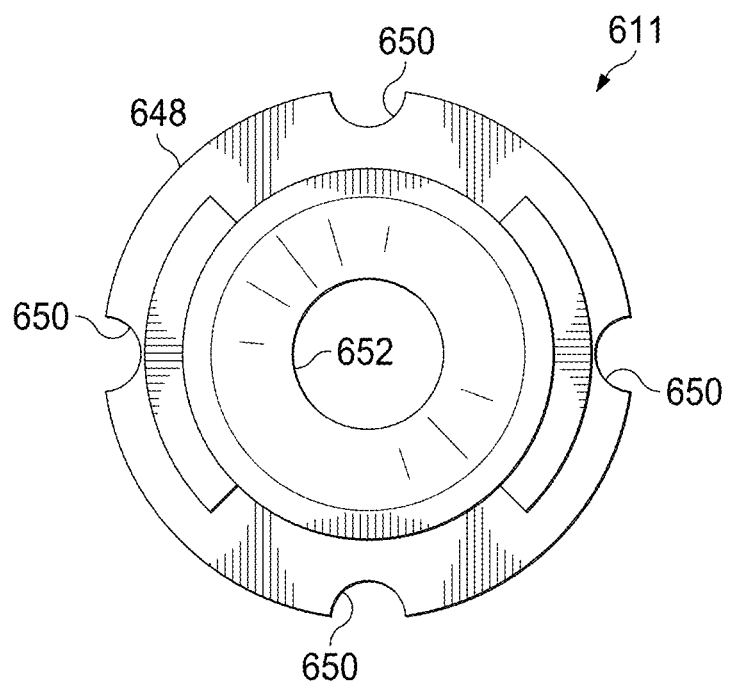
FIG. 6F is a top view of an alternate embodiment of an anchoring device.

Referring to FIGS. 6E and 6F, an alternate embodiment of cannulated locking screw 611 of an anchoring device will be described. Screw 611 has self-tapping right-handed threads 643. Flange 648 is adjacent the threads and limits the depth screw 611 can penetrate into the bone. Flange 648 contains four detent indentions 650 which engage with insertion tool 1400. Screw 611 contains a recess 646 which engages collet 701 to anchor electrode 500 within lumen 652 of screw 611, lumen 704 of collet 701, and lumen 804 of locking cap 801. In a preferred embodiment, the recess is frustoconical in shape, having an incline as measured from a central longitudinal axis of between about 25° and about 45°. Other inclines are envisioned. Bayonet mount 644 allows screw 611 to be attached and secured to locking cap 800 by 60° of rotation, as will be further described. Screw 611 is preferably composed of titanium, an alloy thereof, or a suitable medical plastic. The dimensions of locking screw 601 are similar to those of screw 600.

Figure 7A:
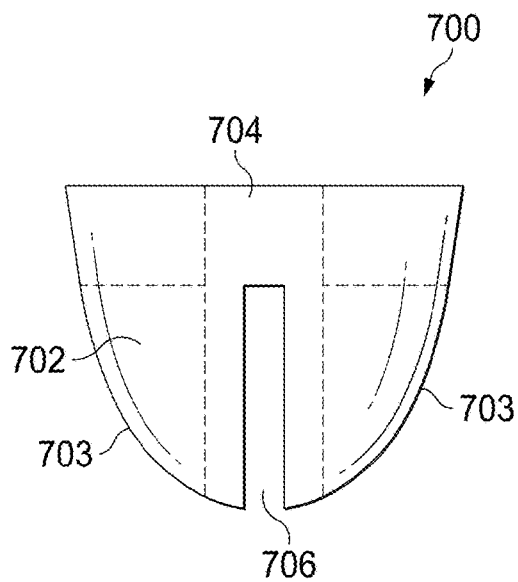
FIG. 7A is a cross section view of a preferred embodiment of a collet.
Figure 7C:
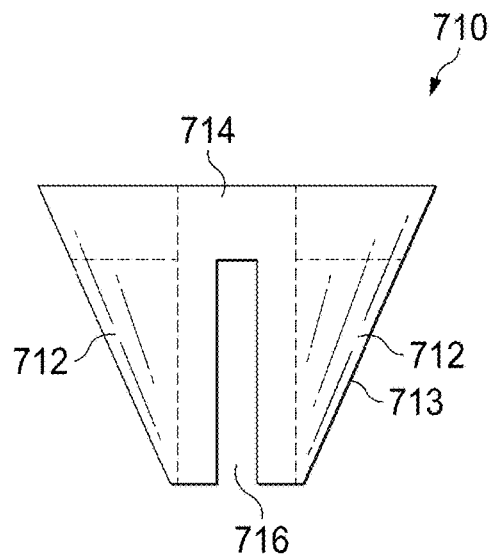
FIG. 7C is a cross section view of a preferred embodiment of a collet.
Figure 7B:
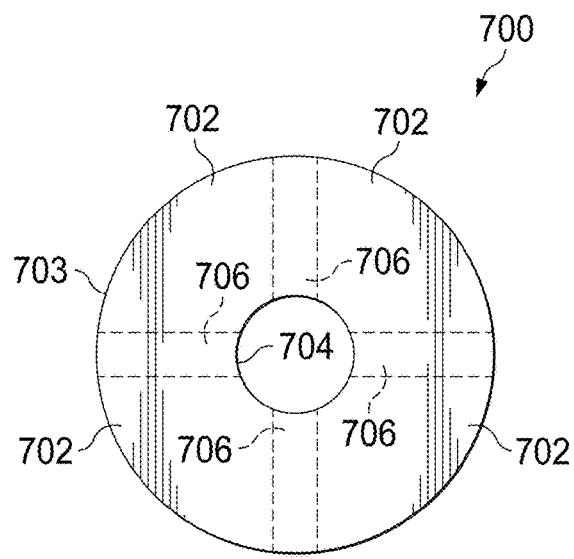
FIG. 7B is a top view of a preferred embodiment of a collet.

Referring to FIGS. 7A and 7B, collet 700 is fabricated from a biocompatible polymer such as polytetrafluoroethylene. Collet 700 has two or more flexible arms 702 separated by slots 706. Four slots are shown. However, between two and eight slots are envisioned in other embodiments. Each of the flexible arms comprises an elliptical outside surface 703 with a minor radius of about 2 mm and a major radius of about 3 mm. The flexible arms of the collet are designed to fit within the recess of the locking screw. The flexible arms are designed to bend inward when the locking cap forces the collet into the recess of the locking screw due to the outside shape of arms and the inside shape of the recess.

Figure 7D:
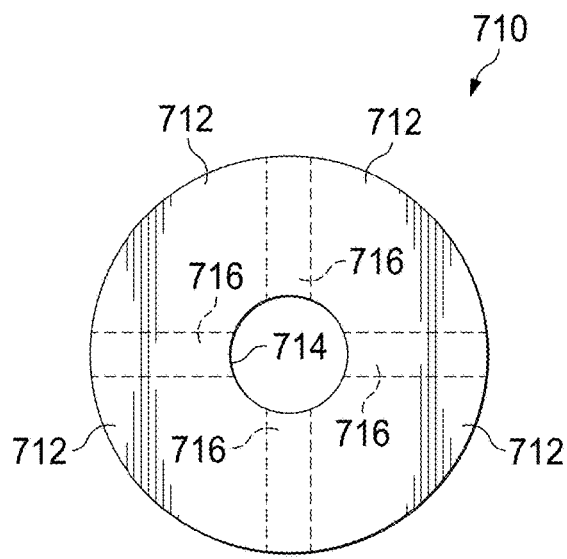
FIG. 7D is a top view of a preferred embodiment of a collet.

In other embodiments, outside shape 713 of the collet may be frustoconical, as shown in FIGS. 7C and 7D. The incline of the outside shape in a preferred embodiment, is about 30°, but may be between about 25° and about 45°. Other inclines are envisioned. Collet 710 includes flexible arms 712, slots 716, and central lumen 714. Collet 710 is designed to mate with recess 646 of locking screw 611.

Figure 8A:
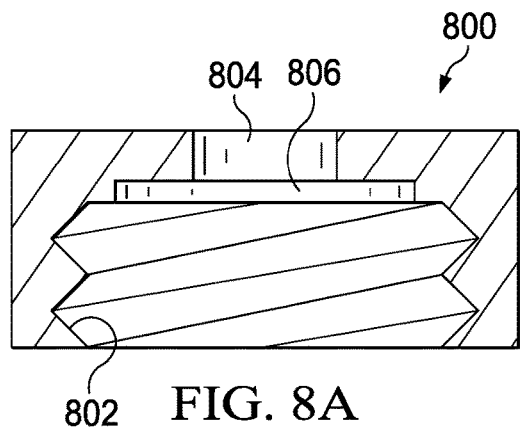
FIG. 8A is a cross section view of a preferred embodiment of a locking cap.
Figure 8C:
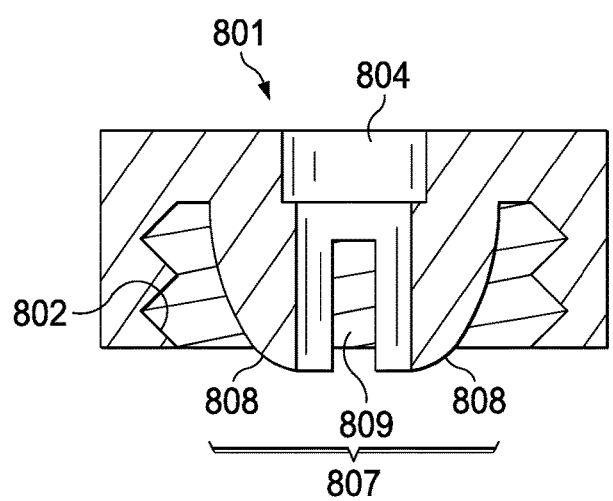
FIG. 8C is a cross section view of an alternate embodiment of a locking cap.
Figure 8B:
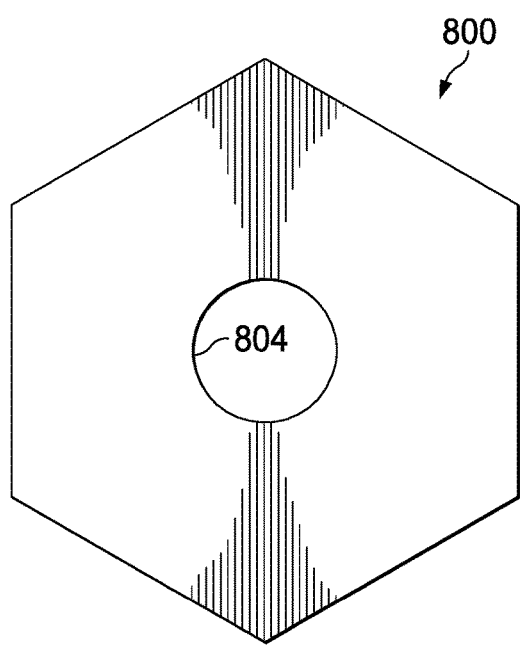
FIG. 8B is a top view of a preferred embodiment of a locking cap.

Referring to FIGS. 8A and 8B, locking cap 800 is described. The outside surface of locking cap 800 preferably designed to fit a standard hex-head spanner to simplify manufacture. Other spanner head shapes can be employed. Locking cap 800 has left-handed threads 802 that are designed to mate with left-handed threads 604 of screw 600 or 601. Locking cap 800 also has a central lumen 804 sized to allow electrode 500 and insertion tool 1400 to pass through. The underside of locking cap 800 has a recessed seat 806 designed to accommodate the outer diameter of the collet. The collet is designed to nest inside recessed seat 806 and be held in place by a press fit tolerance. In a preferred embodiment, the diameter of recessed seat 806 is 6 mm. An inert epoxy may be employed to fix the collet in the seat. Locking cap 800 is preferably composed of titanium or a biologically inert alloy thereof.

Figure 8D:
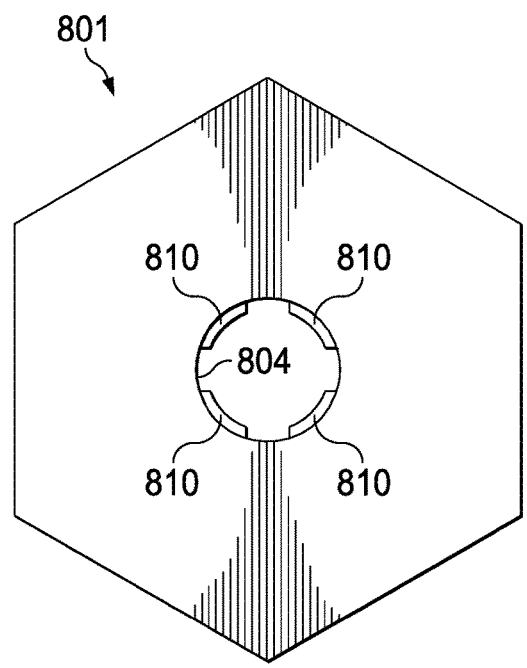
FIG. 8D is a top view of an alternate embodiment of a locking cap.
Figure 8E:
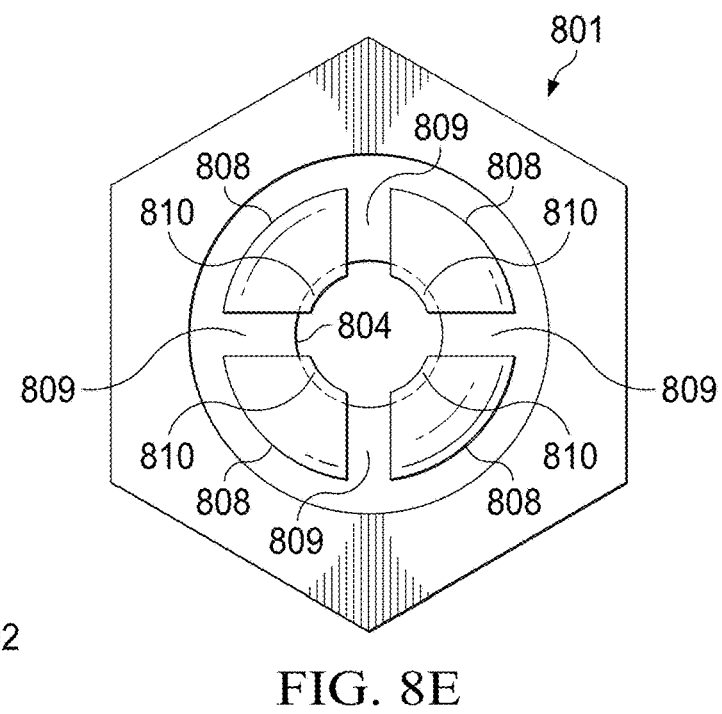
FIG. 8E is a bottom view of an alternative embodiment of a locking cap.

Referring to FIGS. 8C, 8D and 8E, alternate locking cap 801 is described. Locking cap 801 includes an integrally formed elliptical protrusion 807 that matches the shape of recess 606 or 636. The elliptical protrusion includes four flexible arms 808 separated by slots 809. Other numbers of arms and slots are envisioned, as required. Lumen 804 extends through the top of locking cap 800 to the tip of elliptical protrusion 808, culminating in one or more teeth 810. Teeth 810 protrude from and are integrally formed with the flexible arms. The teeth extend radially inward into lumen 804. When assembled and implanted, the flexible arms are forced inward by the recess and clamp electrode 500 to prevent electrode migration. In a preferred embodiment, the locking cap is machined from polyoxymethylene or poly-tetrafluoroethylene. In another embodiment, the locking cap can be machined from a titanium alloy.

Figure 8F:
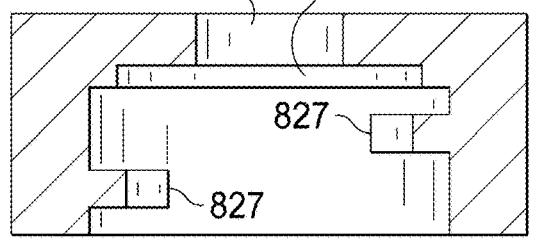
FIG. 8F is a cross section view of a preferred embodiment of a locking cap.
Figure 8G:
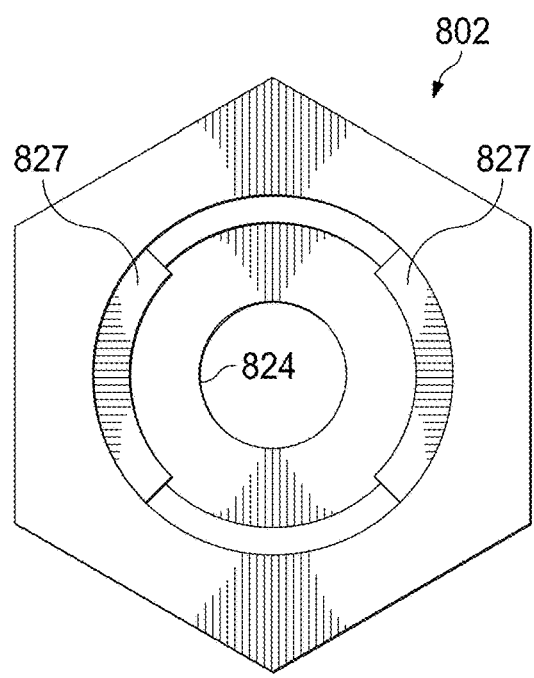
FIG. 8G is a bottom view of a preferred embodiment of a locking cap.

Referring then to FIG. 8G and 8F, an alternate locking cap 802 is described. Locking cap 802 includes bayonet mount 827 that is designed to match bayonet mount 644 of screw 611. Locking cap 802 includes central lumen 824 sized to allow electrode 500 and insertion tool 1400 to pass through. The underside of locking cap 801 includes recessed seat 826 designed to accommodate the outer diameter of the collet. The collet is designed and nest inside recessed seat and be held in place by a pressed fit tolerance. In a preferred embodiment, the diameter of the recessed seat is about 6 mm. In another alternative embodiment, the collet may be fixed within the recessed seat by a suitable medical epoxy. In a preferred embodiment, the locking cap is composed of a titanium alloy.

Figure 9:
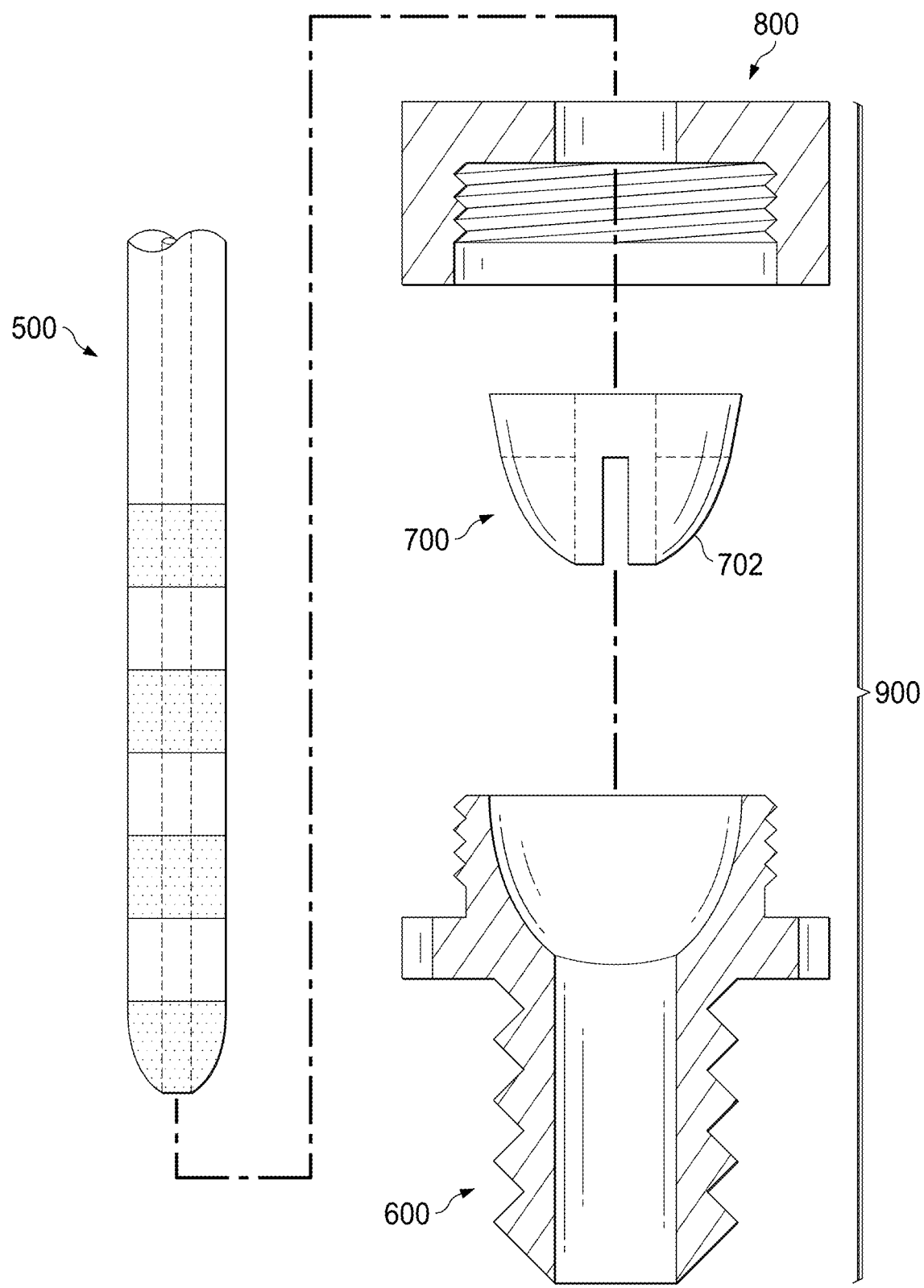
FIG. 9 is an exploded view of a preferred embodiment of an electrode array threaded with an anchoring device.

Referring to FIG. 9, anchoring device 900 includes screw 600, collet 700, and locking cap 800. Electrode 500 is inserted through the central lumen 804 of locking cap 800, central lumen 704 of collet 700, end central lumen 612 of screw 600. When locking cap 800 is tightened, the collet is forced downward into the recess. Flexible arms 702 of collet 700 are then compressed and crimp electrode 500. The friction between the interior of the arms and the exterior of the electrode prevents movement of the electrode, relative to the collet, and the locking screw.

Referring to FIG. 10, Jamshidi (PAK) needle 1000 includes rigid needle 1002, awl tip 1004, and handle 1006. Needle 1000 is sized to fit within guide tube 1100. Rigid needle 1002 allows for piercing the soft tissue between the incision site and the pars interarticularis, and for creating a lead hole in the Pars for insertion of the locking screw.

Referring the FIG. 11, guide tube 1100 includes body 1102, lumen 1104 within body 1102, frustoconical end 1106, and distal tip 1108. In a preferred embodiment, the distal tip is shaped as a reverse ellipse, which forms a concave transition from the cylindrical outside surface to the open lumen. Body 1102 is generally cylindrical and designed to fit within guide tube 1100 with a tolerance sufficient to allow longitudinal movement, but restrict lateral movement. Lumen 1104 has a diameter that is substantially equal to that of rigid needle 1002 of PAK needle 1000. The lumen is sized to allow longitudinal movement, but constrict lateral movement of PAK needle 1000 from guide tube 1100. When needle 1000 is fully inserted into guide tube 1100, the top of guide tube 1100 abuts the bottom of handle 1006 and awl tip 1004 extends from distal tip 1108.

Referring to FIG. 12, guidewire (Kirschner wire) 1200 is of a similar diameter to that of electrode 500. The guidewire, when in use, is placed into the guide hole in the Pars created by the needle. In a preferred embodiment, the guidewire is a titanium alloy of sufficient diameter to fit within lumen 1104 and be visible fluoroscopically. Guidewire 1200 is used to guide screw 600, collet 700, and locking cap 800 to the implantation site prior to the insertion of electrode 500 at the implantation site.

Figure 13:
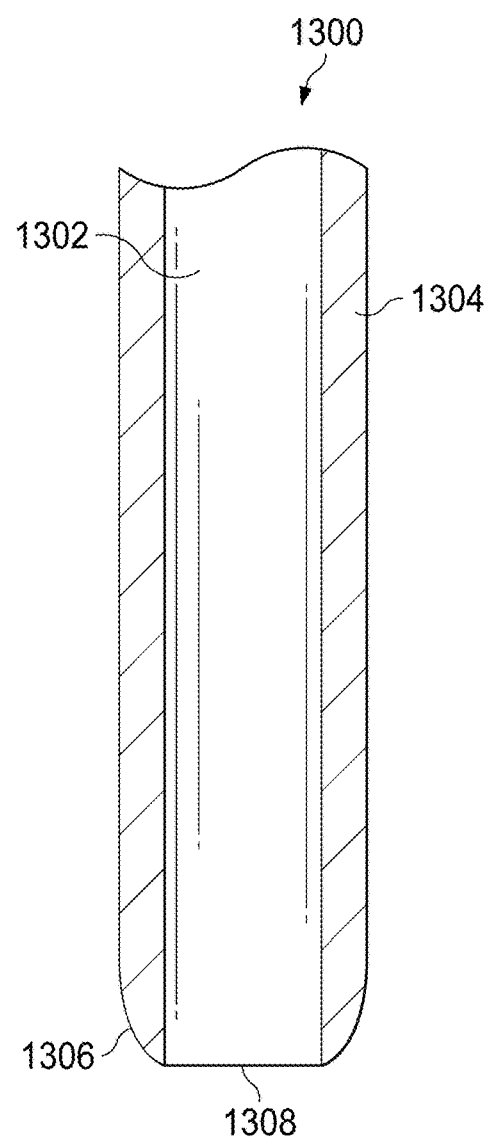
FIG. 13 is a view of a preferred embodiment of a dilator tube used with a preferred embodiment of an anchoring method.

Referring to FIG. 13, dilator tube 1300 includes lumen 1302 within body 1304 and semi-conical nose 1306 at distal tip 1308. The body of dilator tube 1300 is generally cylindrical and is made of rigid non-conducting material such as poly-ether-ether-ketone (PEEK). The lumen is sized to fit the outside diameter of insertion tool 1400 and allow longitudinal movement, but prevent lateral movement. The diameter of distal tip 1308 of dilator tube 1300 is substantially equal to the diameter of flange 608.

Figure 14A:
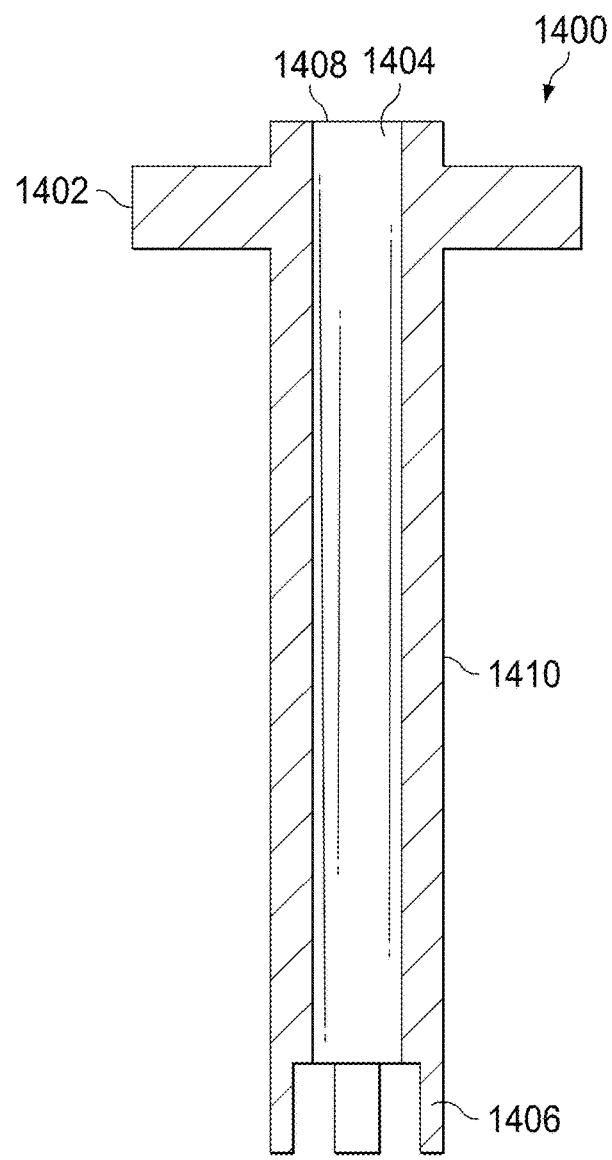
FIG. 14A is a side view of preferred embodiment of an insertion tool used with a preferred embodiment of an anchoring method.
Figure 14B:
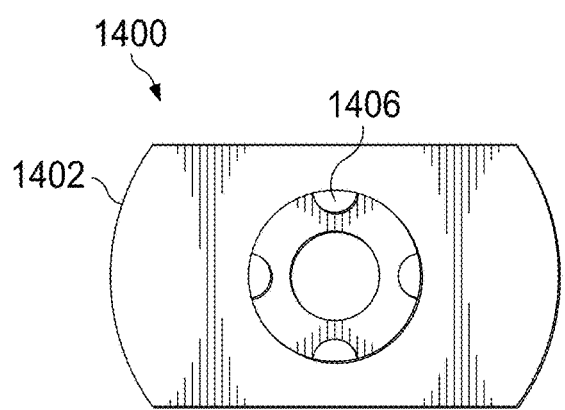
FIG. 14B is a bottom view of a preferred embodiment of an insertion tool used with a preferred embodiment of an anchoring method.

Referring to FIGS. 14A and 14B, insertion tool 1400 includes one or more handles 1402, lumen 1404 within body 1410, and tapered projections 1406. Tapered projections 1406 fit into detent indentions 610 of the locking screw prior to assembly of the screw with the collet and the locking cap. Torque is applied to the insertion tool using handles 1402. Insertion tool 1400 has slightly tapered projections 1406 which engage the detent indentions on the locking screw with a press fit tolerance sufficient to hold the locking screw during the insertion procedure, but release it after the screw is tapped into the Pars. The insertion tool includes stop 1408 which is designed to limit the longitudinal travel of the drill, which will be further described.

Figure 15:
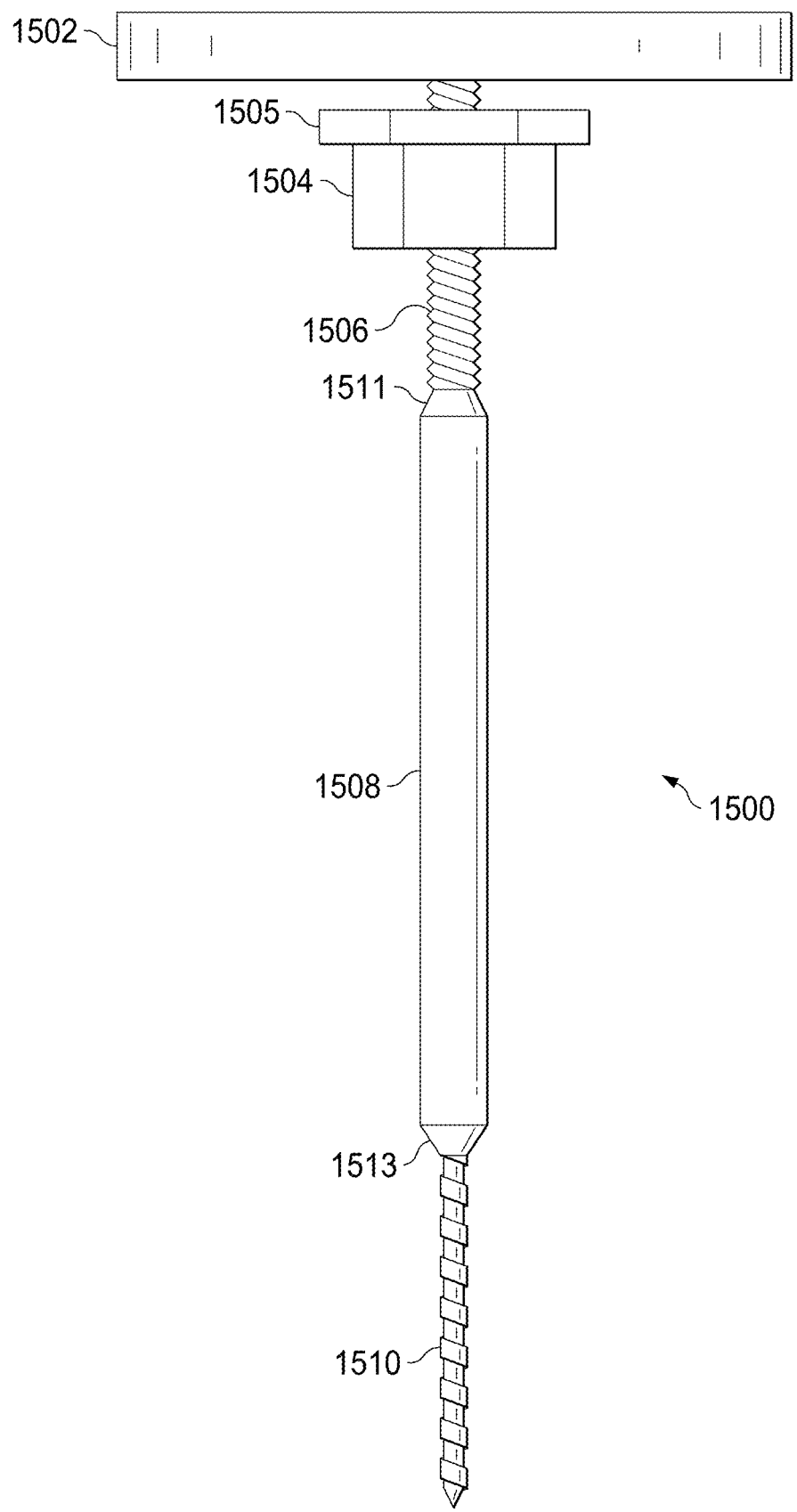
FIG. 15 is a view of a preferred embodiment of a drill a preferred embodiment of an anchoring method.

Referring to FIG. 15, drill 1500 includes handle 1502, depth nut 1504, lock nut 1505, shaft 1508, and drill bit 1510. Shaft 1508 includes diameter reductions 1511 and 1513 to avoid interference with the alignment of the shaft in the lumen of the insertion tool. When drill 1500 is placed into insertion tool 1400, drill 1500 can only be advanced until depth nut 1504 reaches stop 1408 of insertion tool 1400. In a preferred embodiment, left-handed threads 1506 are left-handed to allow for adjustment of depth nut 1504 to control the depth that drill bit 1510 will reach. Looking downward at the tool, rotating depth nut 1504 counterclockwise with respect to shaft 1508 causes depth nut 1504 to move downwards towards shaft 1508 which shortens the maximum depth reachable by drill bit 1510. Conversely, rotating the depth nut clockwise causes depth nut 1504 to move upwards towards handle 1502, thereby increasing the maximum depth reachable by drill bit 1510. The diameter of shaft 1508 corresponds with the diameter of inner lumen 1404 of insertion tool 1400. The diameter of drill bit 1510 corresponds with the inner diameter of the lumen in the locking screw. Lock nut 1505 is advanced to a position adjacent depth nut 1504, and then torqued into a constricted position against the depth nut so that neither can move, thereby allowing the position of depth nut 1504 to be fixed on the threaded shaft.

Figure 16A:
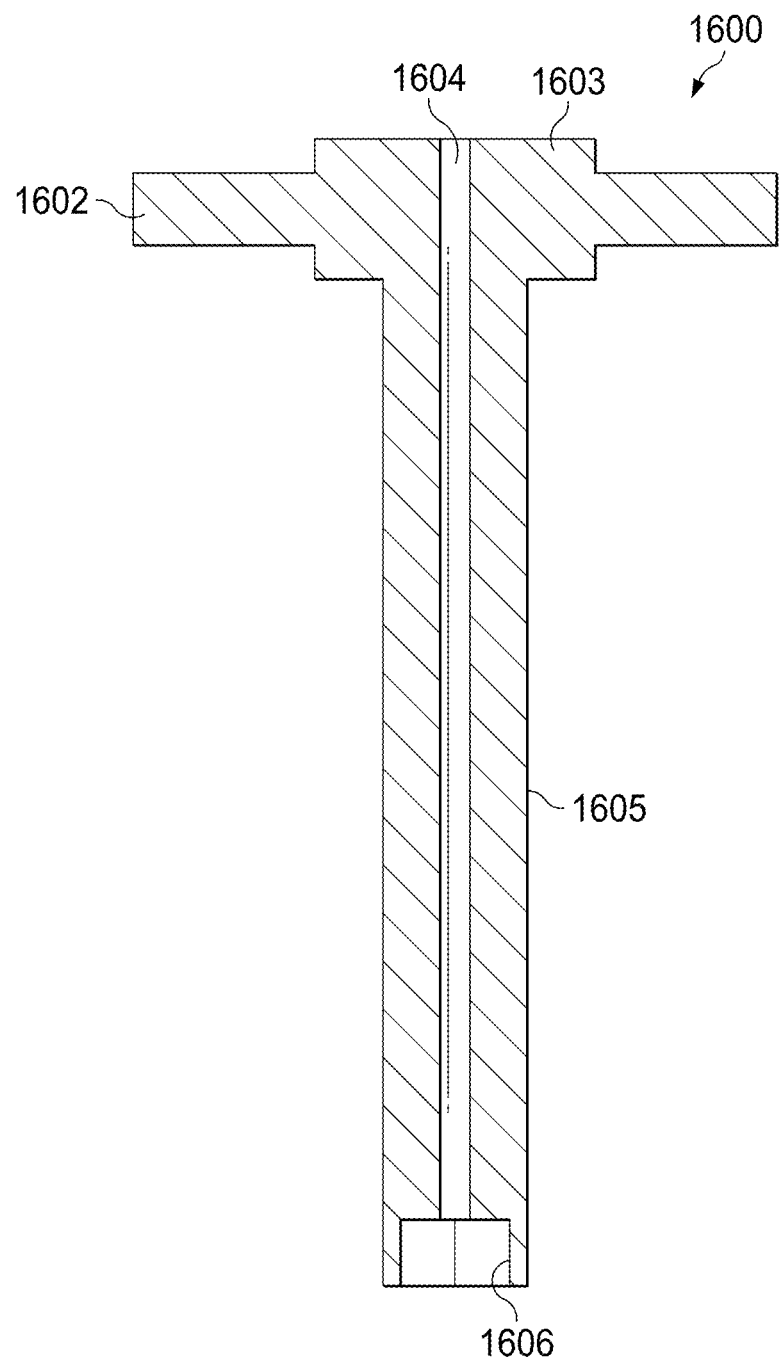
FIG. 16A is a side view of a preferred embodiment of a driver used with a preferred embodiment of an anchoring method.
Figure 16B:
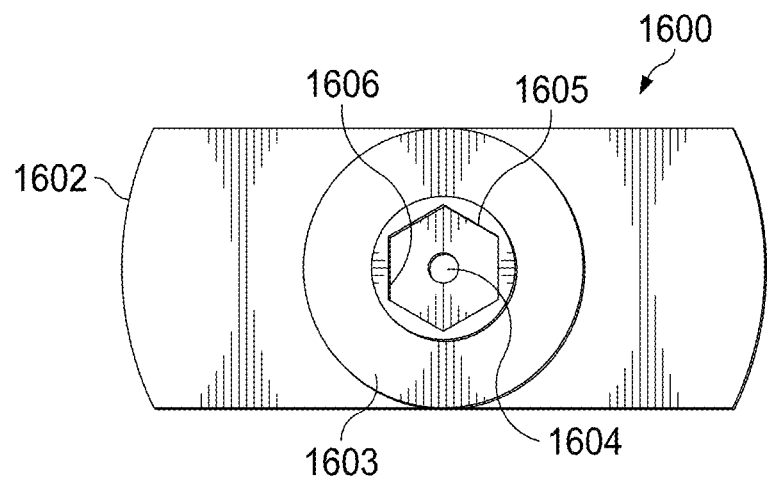
FIG. 16B is a bottom view of a preferred embodiment of a driver used with a preferred embodiment of an anchoring method.

Referring to FIGS. 16A and 16B, locking cap driver 1600 includes handle 1602, lumen 1604, driver head 1606 and driver body 1605. Lumen 1604 allows for threading locking cap driver 1600 onto electrode 500. Driver head 1606 is shaped to fit locking cap 800, which, in a preferred embodiment, is a hexagonal spanner head. Locking cap driver 1600 includes ratchet mechanism 1603. Ratchet mechanism 1603 is torque limited to prevent overtightening locking cap 800 during the installation of the anchoring device. In a preferred embodiment, the torque is limited to approximately 3 ft./lbs. This torque limit may be adjusted. This torque is sufficient to allow locking cap 800 to compress the arms of collet 700, but yet prevent extraction of screw 600. In a preferred embodiment, driver body 1605 is made of a rigid plastic such as poly-ether-ether-ketone (PEEK) to allow radiolucency. In another preferred embodiment, driver body 1605 is made of titanium alloy for situations where exacting torque or angular placement are required. In a preferred embodiment, the ratchet is reversible so that the tool may be used to extract the locking screw if need be.

In another preferred embodiment, locking cap driver 1600 can be provided as two separate tools, one which only provides torque in a clockwise direction so that the only use is to insert the anchoring device and another which only provides torque in a counterclockwise direction so that the only use is to extract the anchoring device. By providing two separate tools confusion may be reduced, thereby preventing unintentional over insertion of the anchoring device into the pars during an extraction procedure.

Figure 17:
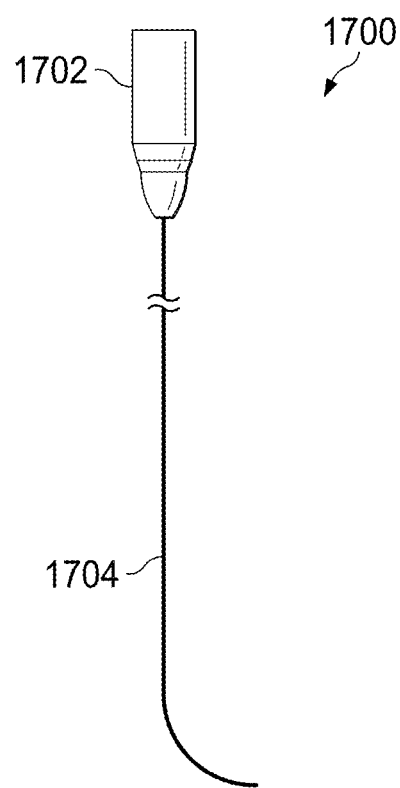
FIG. 17 is a view of a preferred embodiment of a stylet used with a preferred embodiment of an anchoring method.

Referring to FIG. 17, stylet 1700 includes handle 1702 and bend 1704. Stylet 1700 is sized to fit within stylet channel 504 of electrode 500. In a preferred embodiment, stylet 1700 is made from nickel-titanium. The nickel-titanium alloy possesses a unique crystaline structure that exhibits "superelasticity," allowing stylet 1700 to deform significantly under stress and yet return to its original shape once the stress is released. In a preferred embodiment, stylet 1700 can be formed to have a predetermined curve for locating the electrode 500. Once in this curved shape, the stylet 1700 can be straightened in order to be inserted through the straight lumen 1604 of locking cap driver 1600. Once the tip of stylet 1700 emerges from screw 600 in the intervertebral foramen, the alloy returns to its curved shape, thereby positioning the tip of the electrode 500 parallel to the nerve root and facilitating location of the electrode 500 peripheral to the dorsal root ganglion.

Figure 18:
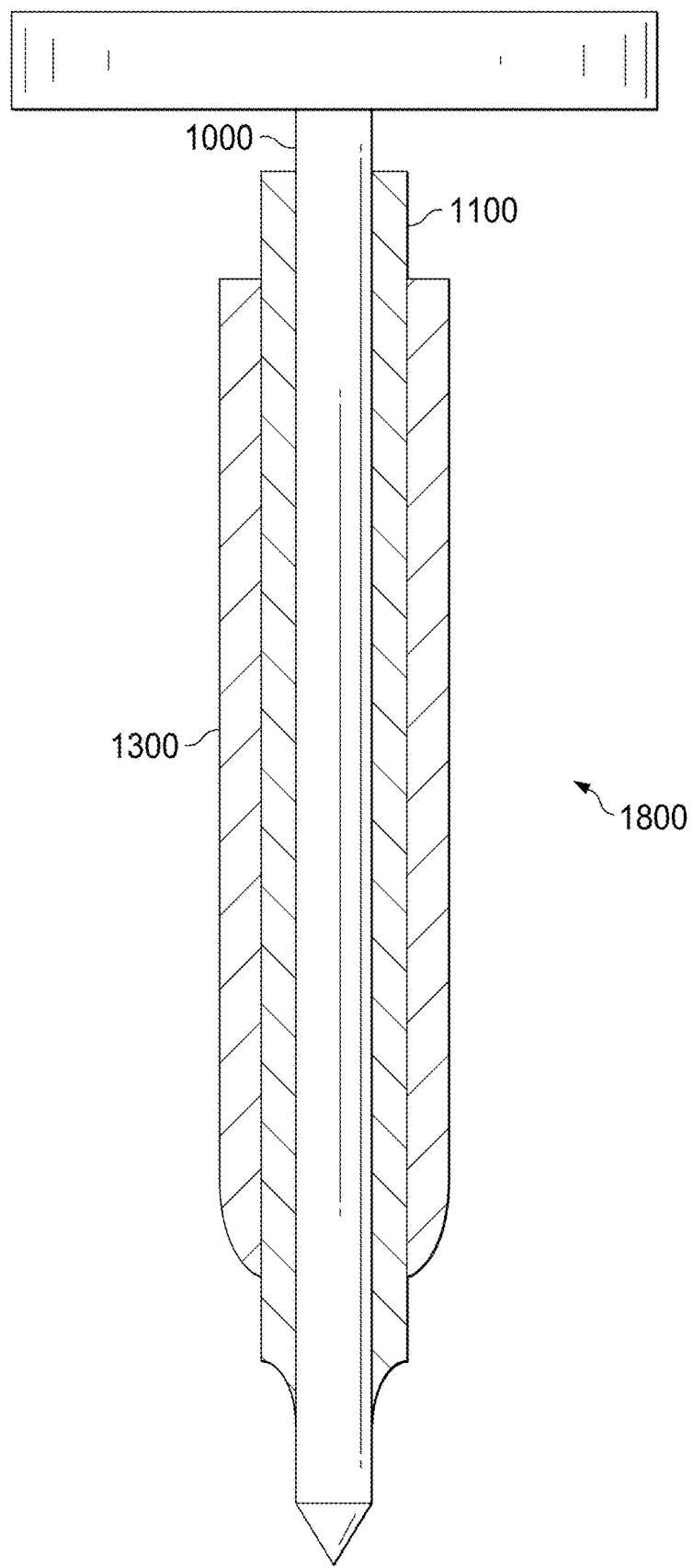
FIG. 18 is a cutaway view of a preferred embodiment of an assembled tool set comprising a dilator tube, a guide tube, and a needle.

Referring to FIG. 18, assembled tool 1800 will be described. Assembled tool 1800 includes dilator tube 1300, guide tube 1100, and needle 1000. Dilator tube 1300 has lumen 1302 with a diameter corresponding to the outer diameter of guide tube 1100, allowing guide tube 1100 to be inserted into dilator tube 1300. In a preferred embodiment, the outer diameter of guide tube 1100 and diameter of lumen 1302 in dilator tube 1300 are about 10 mm. Needle 1000 has an outer diameter corresponding to the inner diameter of guide tube 1100, allowing needle 1000 to be inserted into guide tube 1100. In a preferred embodiment, the outer diameter of needle 1000 and inner diameter of guide tube 1100 are about 2 mm. When assembled, all the parts of the tool should be free to move longitudinally, but yet be substantially coaxial.

Figure 19:
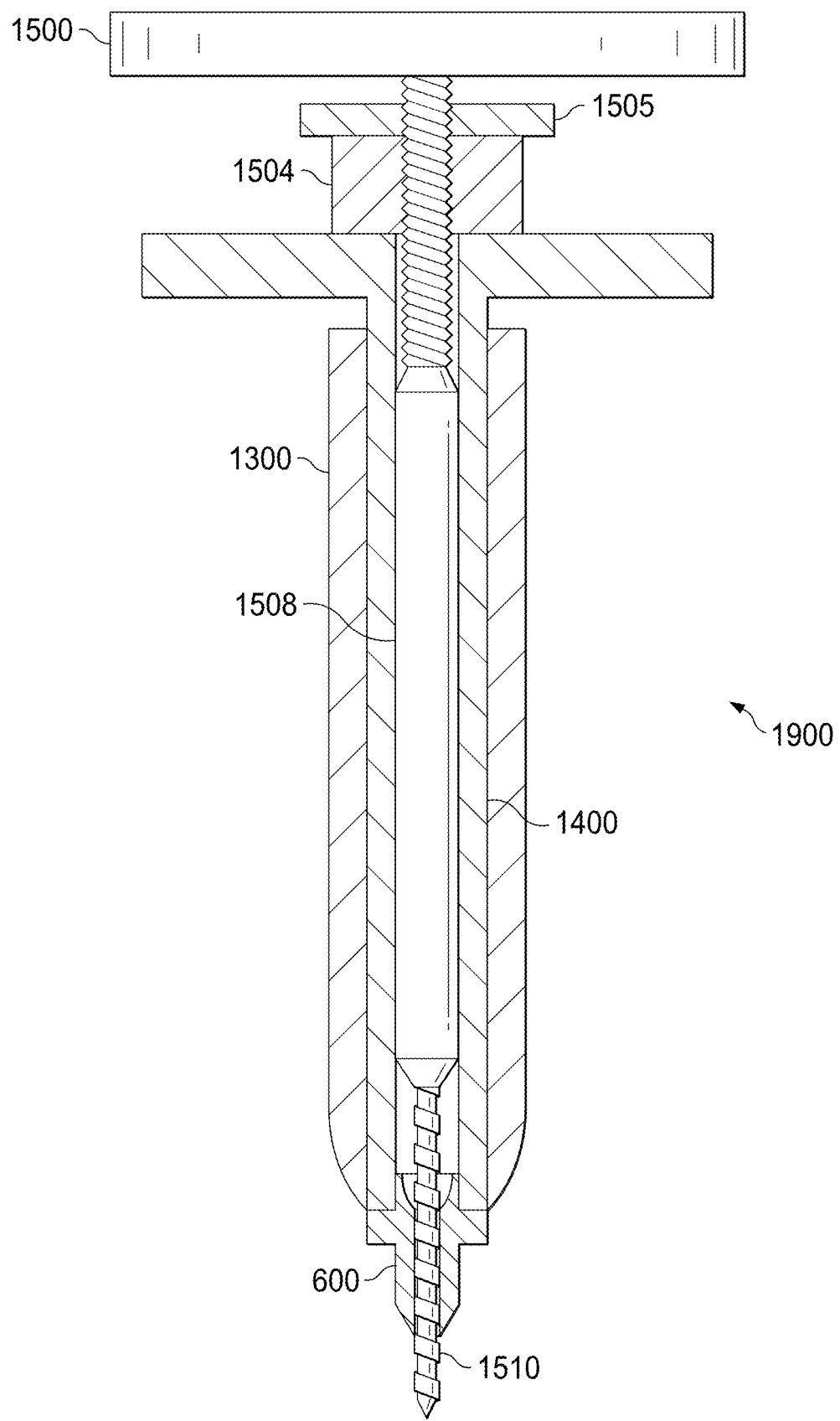
FIG. 19 is a cutaway view of a preferred embodiment of an assembled tool set comprising a dilator tube, an insertion tool, a drill, a depth stop, and an anchoring device.

Referring to FIG. 19, assembled tool 1900 will be described. Assembled tool 1900 includes dilator tube 1300, insertion tool 1400, drill 1500, and screw 600. Insertion tool 1400 has an outer diameter corresponding to the inner diameter of lumen 1302 of dilator tube 1300, allowing insertion tool 1400 into dilator tube 1300. In a preferred embodiment, the outer diameter of insertion tool 1400 is about 10 mm. Insertion tool 1400 has tapered projections 1406 that engage detent indentions 610 of screw 600, allowing insertion tool 1400 to turn screw 600 and advance self-tapping right-handed threads 602 into the pars. Drill 1500 has a shaft 1508 with a diameter corresponding to the inner diameter of lumen 1404 in insertion tool 1400 and a drill bit 1510 that corresponds to the inner diameter of lumen 612 in screw 600. Drill 1500 can therefore be advanced into insertion tool 1400, allowing drill bit 1510 to protrude beyond screw 600 by a distance determined by the adjustment of depth nut 1504 and lock nut 1505. When assembled, all parts of the tool should be free to move longitudinally, but should be held in a substantially coaxial orientation.

Figure 20:
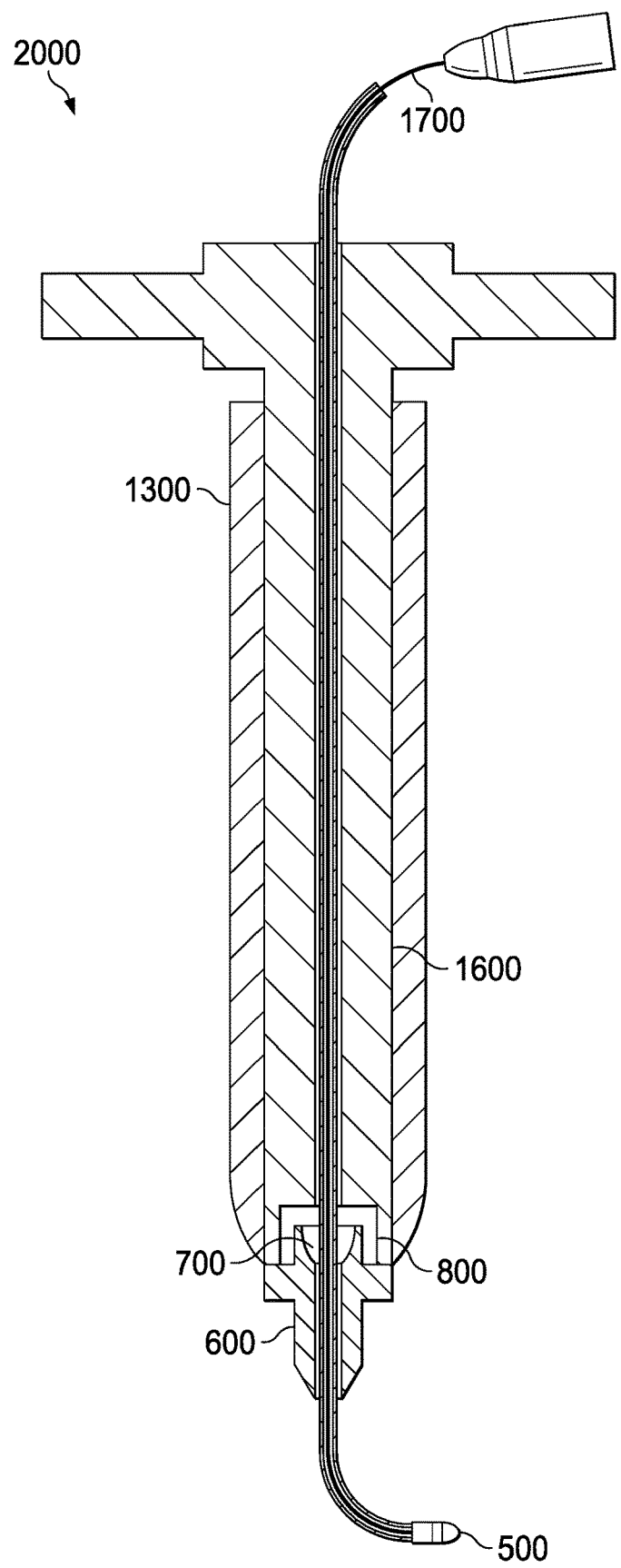
FIG. 20 is a cutaway view of a preferred embodiment of an assembled tool set comprising a dilator tube, a driver, an electrode, a stylet, an anchoring device, a collet, and a locking cap.

Referring to FIG. 20, assembled tool 2000 will be described. Assembled tool 2000 includes dilator tube 1300, locking cap driver 1600, screw 600, collet 700, locking cap 800, electrode 500, and stylet 1700. Locking cap driver 1600 has an outer diameter corresponding to the inner diameter of lumen 1302 in dilator tube 1300. Stylet 1700 is inserted into electrode 500 and used to advance electrode 500 through the lumen 1604 of locking cap driver 1600, through lumen 804 of locking cap 800, through lumen 704 of collet 700, and through lumen 612 of screw 600, into the intervertebral foramen. The collet is fit within the seat of the locking cap. Driver head 1606 engages locking cap 800 and allows locking cap driver 1600 to advance locking cap 800 onto screw 600, causing collet 700 to engage electrode 500. The parts of the assembly tool should be free to move longitudinally, but be substantially coaxial.

Figure 21A:
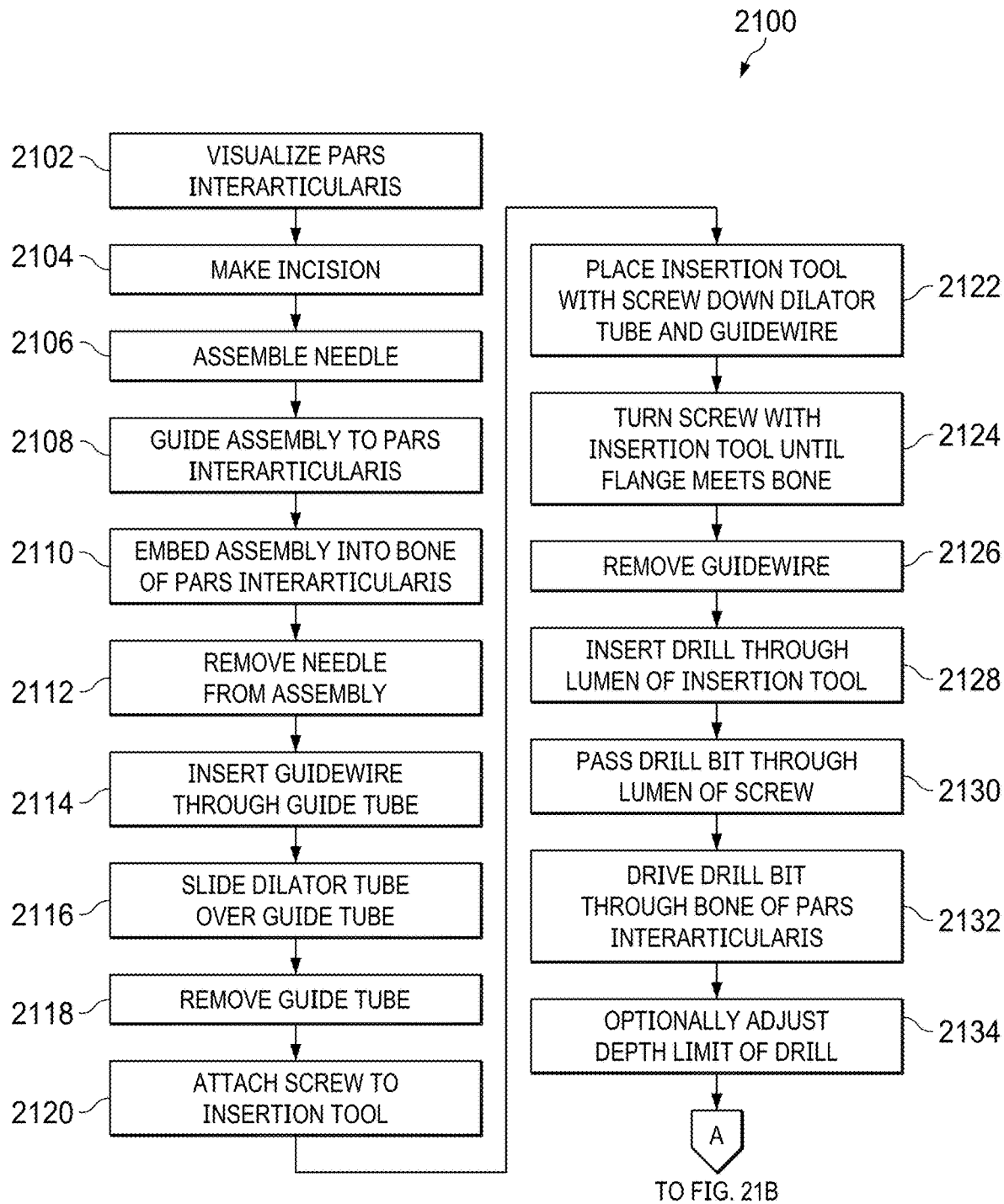
FIGS. 21A and 21B are a flowchart of a preferred embodiment of a method for implanting an anchoring device.
Figure 21B:
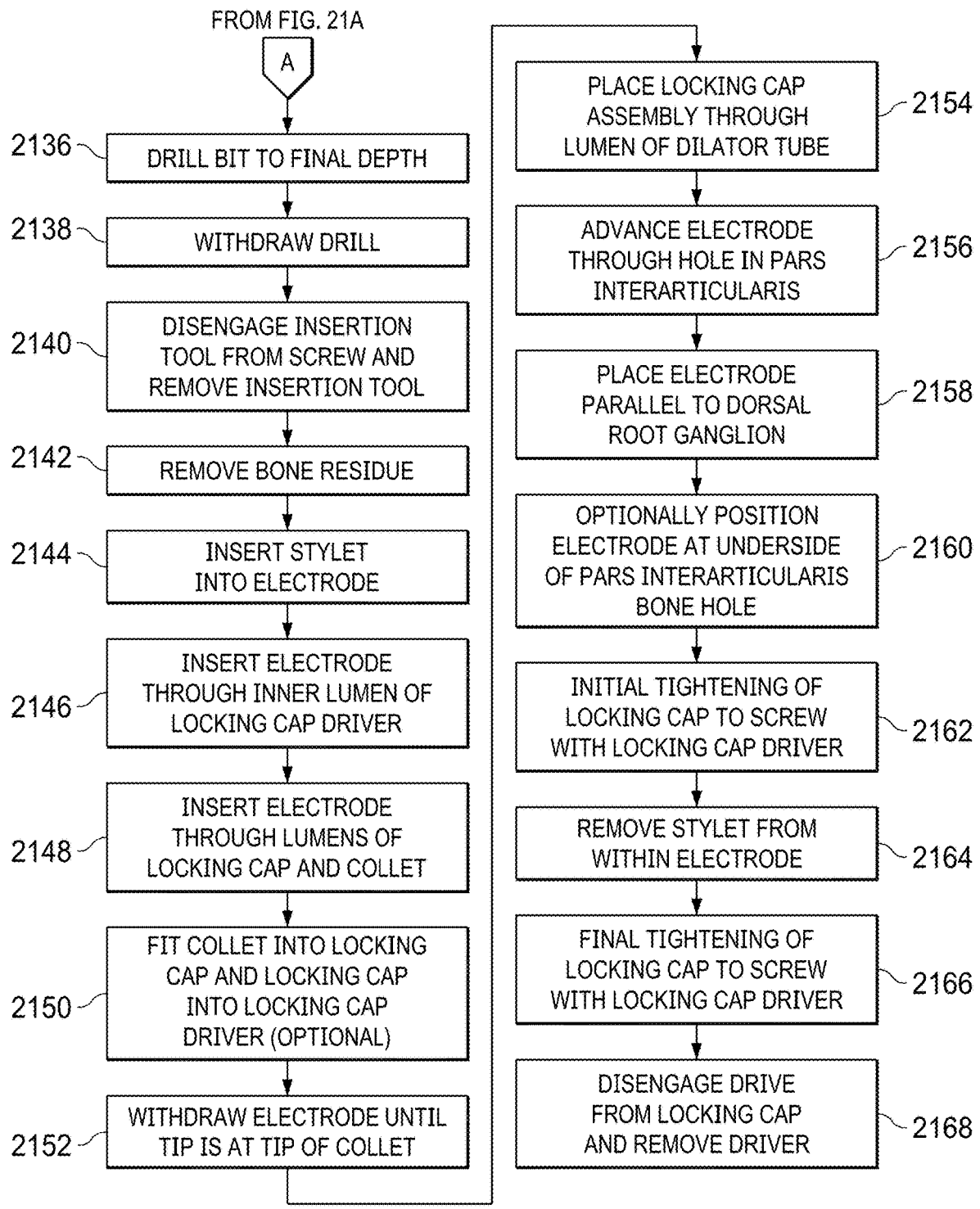

Referring to FIGS. 21A and 21B, method 2100 is used to position electrode 500 next to the spinal nerve root.

At step 2102, both anteroposterior and lateral fluoroscopy are utilized to visualize the pars interarticularis overlying the target nerve root.

At step 2104, a small incision is made in the skin overlying the location of the radiographic projection.

At step 2106, a PAK needle is assembled from needle 1000 and guide tube 1100. Rigid needle 1002 is placed through lumen 1104 of guide tube 1100 by sliding it through lumen 1104 of guide tube 1100.

At step 2108, the assembled tool comprising guide tube 1100 and PAK needle 1000 is inserted into the incision.

At step 2110, handle 1006 is impacted with a mallet to embed awl tip 1004 and the frustoconical end 1106 of guide tube 1100 into the bone of the pars interarticularis.

At step 2112, PAK needle 1000 is then withdrawn.

At step 2114, guidewire 1200 is inserted through lumen 1104 of guide tube 1100.

At step 2116, dilator tube 1300 is then placed over guide tube 1100 until distal tip 1308 meets bone of the pars interarticularis. Semi-conical nose 1306 allows passage through muscle tissue. Dilator tube 1300 is inserted over guide tube 1100 to create a larger opening in the soft tissue around the incision site to make room for implanting screw 600. At step 2118, guide tube 1100 is removed.

At step 2120, screw 600 is attached to insertion tool 1400 by matching detent indentions 610 with tapered projections 1406.

At step 2122, screw 600 and insertion tool 1400 are placed down the lumen 1302 of dilator tube 1300 with the central lumen 612 of screw 600 passing along guidewire 1200.

At step 2124, insertion tool 1400 is manually rotated clockwise using handles 1402 to engage self-tapping screw right-handed threads 602 of screw 600 into the hole in the bone made by awl tip 1004 and guide tube frustoconical end 1106. The screw 600 is then advanced until flange 608 meets the bone. Flange 608 centers dilator tube 1300 as the flange 608 impinges upon the inner lumen 1302 of dilator tube 1300.

At step 2126, guidewire 1200 is removed from screw 600 and dilator tube 1300.

At step 2128, drill 1500 is then inserted through lumen 1404 of insertion tool 1400.

At step 2130, drill bit 1510 at a distal tip of drill 1500 passes through lumen 612 of screw 600.

At step 2132, drill 1500 is rotated clockwise using handle 1502 to drive drill bit 1510 through the bone of the pars interarticularis.

At step 2134, depth nut 1504 is adjusted as a mechanical stop against stop 1408 of insertion tool 1400. Left-handed thread 1506 allows depth nut 1504 to be adjusted without self-advancing as drill 1500 is turned clockwise. The mechanical stop is a safety mechanism to prevent drill 1500 from advancing too far into insertion tool 1400 and to prevent drill bit 1510 from damaging the spinal nerve root. Lock nut 1505 is then advanced into a locking position against the depth nut.

At step 2136, drill bit 1510 is advanced into the bone to its final depth. The final depth is determined by examination of the lateral fluoroscopic visualization, or by stimulated electromyographic (EMG) recording of the underlying nerve root. In the latter case, the cathode of a pulsed current source is attached to drill 1500 which is insulated by dilator tube 1300. The current source anode is attached to the body at a remote location. An example current source waveform might be a square wave with amplitude 7 mA, frequency 1 Hz, pulse duration 500 microseconds. As drill bit 1510 breaches the underlying cortex of the pars interarticularis, the current density becomes sufficient to stimulate the underlying nerve root and elicit an electromyographic response.

At step 2138, drill 1500 is withdrawn.

At step 2140, insertion tool 1400 is disengaged from screw 600 and removed, leaving dilator tube 1300 in place.

At step 2142, bone residue is removed through irrigation and suction via lumen 1302 of dilator tube 1300.

At step 2144, stylet 1700 is inserted into stylet channel 504 of electrode 500.

At step 2146, electrode 500 with stylet 1700 is inserted through the inner lumen 1604 of locking cap driver 1600.

At step 2148, the distal tip 502 of the electrode 500 is then sequentially inserted through lumen 804 of locking cap 800 and through lumen 704 of collet 700.

At step 2150, in one embodiment, collet 700 is press-fit into locking cap 800 which in turn is press-fit into the driver head 1606 end of locking cap driver 1600. In embodiments where the cap and collet are integrally formed, this step is omitted.

At step 2152, electrode 500 is withdrawn until distal tip 502 is at slot 706 of collet 700.

At step 2154, locking cap driver 1600 with electrode 500, locking cap 800 and collet 700 are then placed through lumen 1302 of dilator tube 1300.

At step 2156, under fluoroscopy the electrode 500 is advanced through screw 600, recess 606, and lumen 612 to exit the under surface of the pars interarticularis through the hole that was previously drilled. The trajectory and position of electrode 500 is then guided under fluoroscopy by advancing stylet 1700 while twisting handle 1702.

At step 2158, the electrode 500 is optimally placed parallel to the dorsal root ganglion to facilitate bipolar stimulation.

Optionally at step 2160, if electrode 500 does not properly drive within the foraminal zone, then distal tip 502 is positioned at the underside of the pars interarticularis bone hole and monopolar stimulation is employed.

At step 2162, the threads of the locking cap are engaged with the threads of the screw. Handle 1602 of locking cap driver 1600 is turned counter-clockwise to tighten the locking cap. This compresses the collet against the screw and the recess to drive the flexible arms of the collet against the electrode, which locks the electrode into position. The initial tightening prevents movement of the electrode, but is still light enough that the stylet can be removed from the electrode.

At step 2164, after the electrode 500 is in optimal position and locking cap 800 has been initially tightened, the stylet 1700 is removed.

At step 2166, a final tightening of the locking cap to the screw is performed with locking cap driver 1600. The ratchet is advanced until the torque limit is triggered, thereby forcing the flexible arms of the collet inward, further into the lumen and compressing the electrode exterior. Removal of stylet 1700 allows for additional compression of electrode 500 and further reduces the ability of electrode 500 to slip with respect to screw 600.

At step 2168, Locking cap driver 1600 and dilator tube 1300 are then removed.

Figure 22:
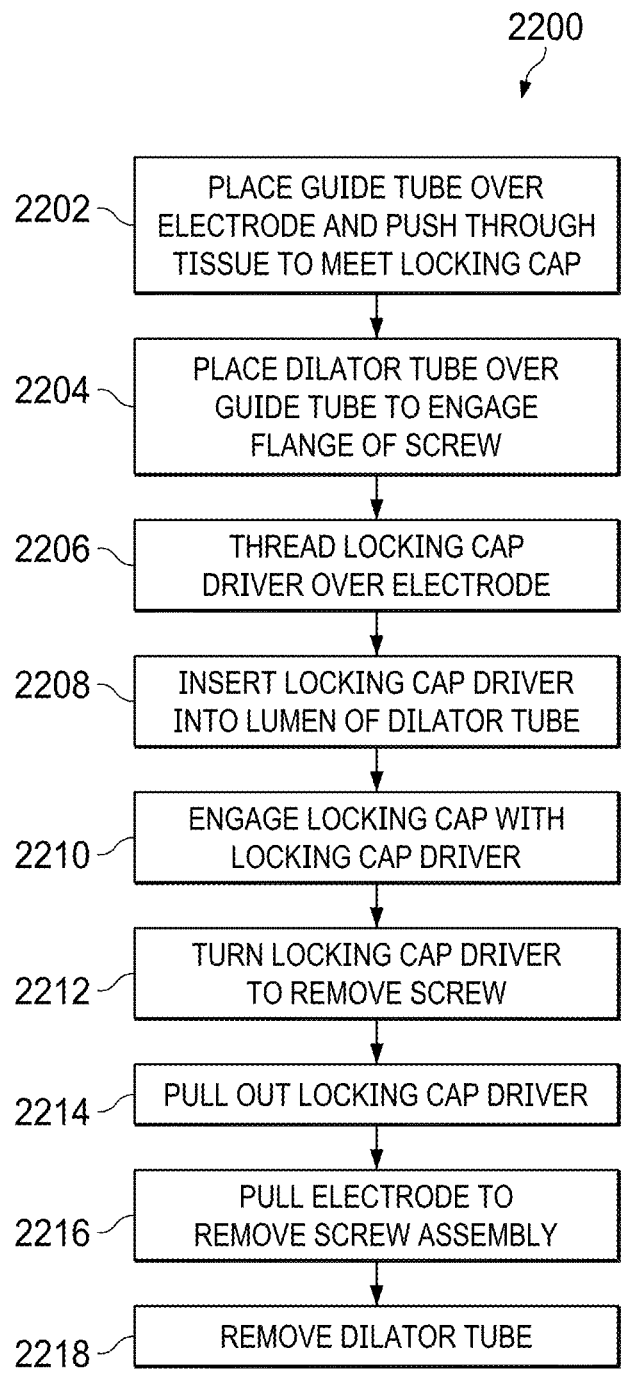
FIG. 22 is a flowchart of a preferred embodiment of a method for removing an anchoring device.

Referring to FIG. 22, method 2200 allows for the electrode and screw assembly to be removed when necessary.

At step 2202, guide tube 1100 is placed over electrode 500 and pushed through the soft tissue until distal tip 1108 of guide tube 1100 meets locking cap 800.

At step 2204, dilator tube 1300 is then placed over guide tube 1100 to engage flange 608 of screw 600.

At step 2206, stainless steel locking cap driver 1600 is threaded over electrode 500.

At step 2208, locking cap driver 1600 is inserted into lumen 1302 of dilator tube 1300.

At step 2210, locking cap driver 1600 engages hex-head locking cap 800.

At step 2212, handle 1702 of locking cap driver 1600 is not torque-limited and is turned counter-clockwise to remove screw 600 from the pars interarticularis.

At step 2214, locking cap driver 1600 is then extracted.

At step 2216, electrode 500 is grasped and pulled. Electrode 500 is still secured by the force of locking cap 800 and screw 600 onto collet 700 that is pinching electrode 500. Pulling electrode 500 applies a force to screw 600 removing the anchoring device, locking cap 800, collet 700, and electrode 500 from the implantation location.

At step 2218, the dilator tube 1300 is then removed.

Figure 23:
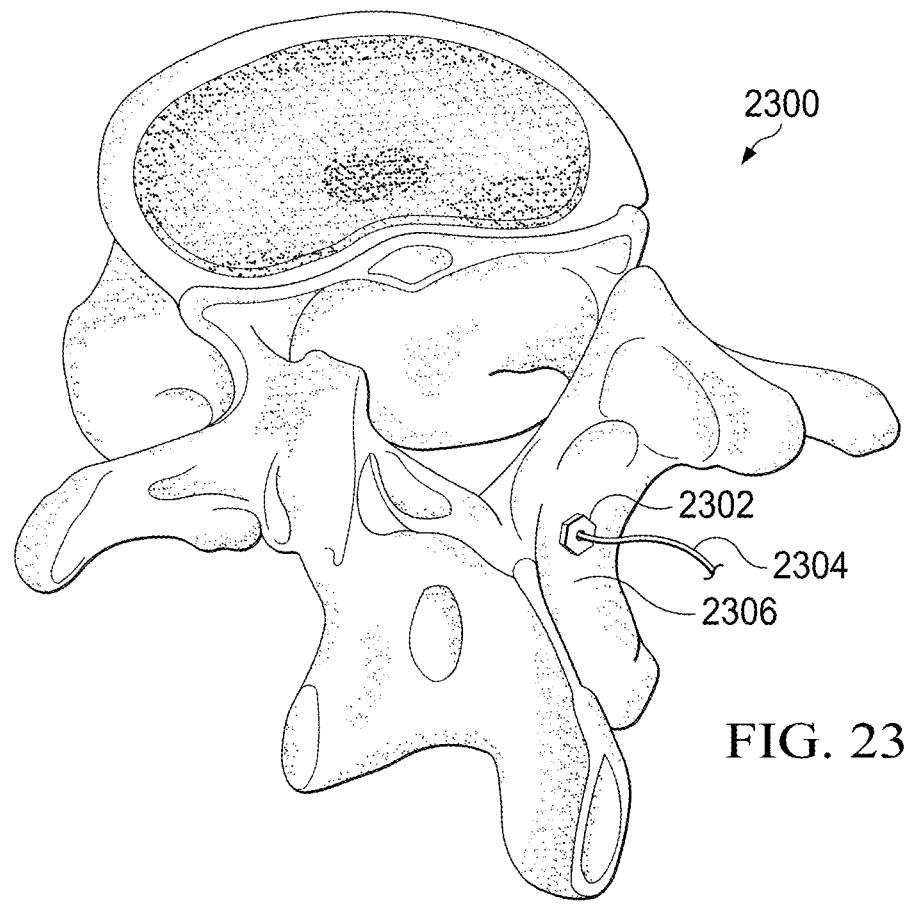
FIG. 23 is an oblique view of a lumbar vertebra with the anchoring device fixed to the bone of the Pars.

Referring to FIG. 23, a representative lumbar vertebra 2300 is shown. Anchoring device 2302 is shown installed in pars interarticularis 2306 as described above. The anchoring device is shown holding electrode 2304 in place to prevent migration.

Figure 24:
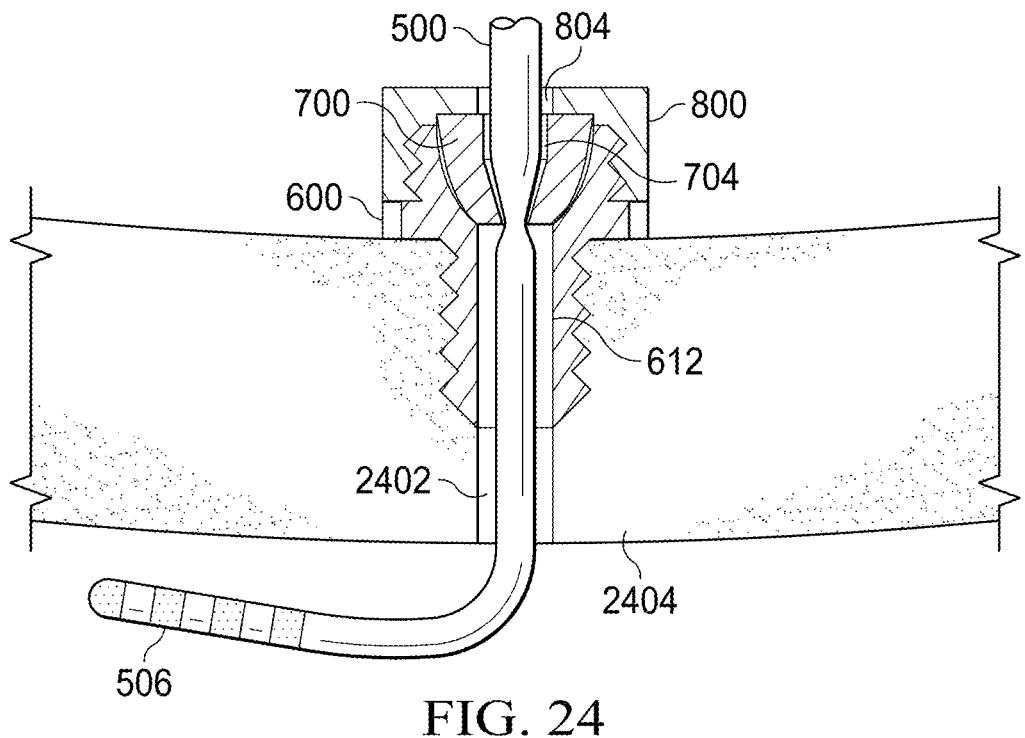
FIG. 24 is a cutaway view of a lumbar vertebra and the anchoring device showing the anchoring device in place.

FIG. 24 shows a cross sectional view of the pars interarticularis in which the anchoring device is installed. Electrode 500 extends through lumen 804 of locking cap 800, lumen 704 of collet 700, lumen 612 of screw 600, and through hole 2402 in pars interarticularis 2404 drilled by drill 1500. Electrode contacts 506 are placed inside the intervertebral foramen adjacent the root ganglion. The force exerted on collet 700 by locking cap 800 forces the flexible arms of the collet into the recess, thereby causing them to move together and exert a frictional clamping force on the electrode.

It will be appreciated by those skilled in the art that modifications can be made to the embodiments disclosed and remain within the inventive concept. Therefore, this invention is not limited to the specific embodiments disclosed, but is intended to cover changes within the scope and spirit of the claims.

The invention claimed is:

1. A method for implanting an anchoring device configured to anchor an electrode to a pars interarticularis over a dorsal root ganglion, the electrode configured to stimulate the dorsal root ganglion, the method comprising:

inserting a screw of the anchoring device into bone of the pars interarticularis;

placing the electrode through the screw into one of a set of positions with respect to the dorsal root ganglion; and, driving a locking cap of the anchoring device onto the screw, the locking cap applying a force onto a collet of the anchoring device in a recess of the screw to lock the electrode into place with respect to the dorsal root ganglion.

2. The method of claim 1, further comprising:
visualizing the pars interarticularis;
creating an incision;
creating a needle assembly by inserting a rigid needle into a lumen of a guide tube; and,
guiding the needle assembly through the incision to the pars interarticularis.

3. The method of claim 2, further comprising:
embedding an awl tip of the rigid needle and a sharp end of the guide tube into bone of the pars interarticularis and creating a hole in the bone; and,
removing the rigid needle from the guide tube.

4. The method of claim 2, further comprising:
inserting a guidewire through the lumen of the guide tube;
placing a dilator tube by sliding the dilator tube over the guide tube until the dilator tube meets the bone of the pars interarticularis; and, removing the guide tube after placing the dilator tube.

5. The method of claim 4, further comprising:
attaching the screw of the anchoring device to an insertion tool and inserting the guidewire into a lumen of the screw; and,
inserting the screw using the insertion tool into a lumen of the dilator tube until the screw meets the bone of the pars interarticularis.

6. The method of claim 5, further comprising:
turning the insertion tool in a first direction to drive the screw into the bone of the pars interarticularis by engaging a first set of screw threads of the screw with the hole until a flange of the screw meets the bone.

7. The method of claim 6, further comprising:
removing the guidewire from the screw and dilator tube.

8. The method of claim 6, further comprising:
inserting a drill through a lumen of the insertion tool until a bit at a distal tip of the drill passes through the screw and meets remaining bone of the pars interarticularis; and,
turning the drill in the first direction and driving the bit into the remaining bone.

9. The method of claim 7, further comprising:
adjusting a mechanical stop at a proximal end of the insertion tool.

10. The method of claim 8, further comprising:
drilling through remaining bone in the pars interarticularis by turning the drill in the first direction and driving the bit through the remaining bone; and,
withdrawing the drill from the insertion tool.

11. The method of claim 9, further comprising:
removing bone residue by providing irrigation and suction; and,
disengaging the insertion tool from the screw and removing the insertion tool from the dilator tube.

12. The method of claim 10, further comprising:
inserting a stylet into a channel of the electrode;
inserting the electrode with the stylet through a lumen of a locking cap driver; and, inserting the electrode through a lumen of the locking cap of the anchoring device and a lumen of the collet of the anchoring device.

13. The method of claim 12, further comprising:

placing locking cap driver with the electrode, the locking cap, and the collet through the lumen of the dilator tube;

placing the electrode in one position of a set positions, a first position of the set of positions having the electrode parallel to the dorsal root ganglion to facilitate bipolar stimulation, and a second position of the set of positions having the electrode at an underside of the hole in the bone of the pars interarticularis to facilitate monopolar stimulation; and, removing the stylet from the electrode after placing the electrode.

14. The method of claim 12, further comprising:

fitting the collet into the locking cap and fitting the locking cap into the locking cap driver; and, sliding the electrode until a distal tip of the electrode is at a distal tip of the collet.

15. The method of claim 14, further comprising:

turning the locking cap driver in a second direction, opposite from the first direction, to engage a set of threads of the locking cap with a second set of screw threads of the screw, to compress the collet into a recess of the screw, and to lock the electrode in place with respect to the anchoring device; and, removing the locking cap driver and the dilator tube.

* * * * *